US006312684B1

(12) United States Patent
Baserga et al.

(10) Patent No.: US 6,312,684 B1
(45) Date of Patent: *Nov. 6, 2001

(54) METHOD OF INDUCING RESISTANCE TO TUMOR GROWTH

(75) Inventors: Renato Baserga, Ardmore; David Abraham, Wynnewood; Mariana Resnicoff, Philadelphia, all of PA (US)

(73) Assignee: Thomas Jefferson University

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/864,641

(22) Filed: May 29, 1997

Related U.S. Application Data

(63) Continuation-in-part of application No. 08/340,732, filed on Nov. 16, 1994, now Pat. No. 5,714,170, and a continuation-in-part of application No. PCT/US95/14952, filed on Nov. 15, 1995.

(51) Int. Cl.[7] .......................... A61K 48/00; A61K 35/00

(52) U.S. Cl. ................... 424/93.21; 514/44; 424/93.1; 424/573; 424/422; 424/423; 424/424; 424/425; 424/93.7; 604/890.1

(58) Field of Search ........................ 424/93.1, 93.21, 424/573, 422, 423, 424, 425, 93.7; 604/890.1; 514/44

(56) References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/172.3 |
| 5,077,059 | 12/1991 | Mishima et al. | 424/573 |
| 5,139,941 | 8/1992 | Muzyczka et al. | 435/172.3 |
| 5,173,414 | 12/1992 | Lebkowski et al. | 435/172.3 |
| 5,252,479 | 10/1993 | Srivastava | 435/235.1 |
| 5,262,308 | 11/1993 | Baserga | 435/69.1 |
| 5,272,082 | 12/1993 | Santoli et al. | 435/240.2 |
| 5,354,674 | 10/1994 | Hodgson | 435/172.3 |
| 5,354,678 | 10/1994 | Lebkowski et al. | 435/172.3 |
| 5,399,346 | 3/1995 | Anderson et al. | 424/93.21 |
| 5,460,831 | 10/1995 | Kossovsky et al. | 424/493 |

FOREIGN PATENT DOCUMENTS

| | | |
|---|---|---|
| WO 91/17253 | 11/1991 | (WO) . |
| WO 92/22486 | 10/1994 | (WO) . |
| WO 97/37010 | 10/1997 | (WO) . |
| WO 99/23259 | 5/1999 | (WO) . |

OTHER PUBLICATIONS

James, W. (1991) Antiviral Chem. & Chemotherapy, vol. 2 (4), 191–214.*
Lieberthal et al. (1996) Am. J. Phys., vol. 271 (3 Part 2), F477–F488*
Lavin et al. (1996) Experientia, vol. 52 (10–11), 979–994.*
Mandelboim et al. (1994) Nature, vol. 369, 67–71, May 1994.*
Huybrechts et al. (1979) Scand. J. Haem., vol. 23 (3), 223–226.*
Hoeltzer et al. (1984) Blut, vol. 48 (4), 233–238.*
Resnicoff, M. et al., "Regression of C6 rat brain tumors by cells expressing an antisense insulin–like growth factor I receptor RNA," *J. Exp. Therap. Oncol.*, 1996, 1, 385–389.
Lahm, H. et al., "Growth Inhibition of Human Colorectal Carcinomas by a Monoclonal Antibody Directed Against the IGF–1 Receptor," *Eur. J. Cancer*, 1991, 27(Suppl. 3), Abstract No. 11.053.
Pietrzykowski, Z. et al., "Inhibition of Growth of Prostatic Cancer Cell Lines by Peptide Analogues on Insulin–like Growth Factor 1," *Cancer Res.*, 1993, 53, 1102–1106.
Pietrzykowski, Z. et al., "Autocrine Growth of Cells Overexpressing the Human IGF–1 and IGF–1 Receptor Genes," *Federal of American Society for Experimental Biology*, 75th Annual Meeting, Atlanta, GA, 1991, Part 3, Abstract No. 7268.
Rohlik, Q. et al., "An Antibody to the Receptor for Insulin–like Growth Factor 1 Inhibits the Growth of MCF–7 Cells in Tissue Culture," *Biochem. Biophys. Res. Commun.*, 1987, 149(1), 276–281.
Shapiro, D. N. et al., "Antisense–mediated reduction in insulin–like growth factor–1 receptor expression suppresses the malignant phenotype of a human rhabdomyosarcoma," *Cancer Res.*, Eighty–Third Annual Meeting, 1992, 33, Abstract No. 2112.
Wickstrom, E. et al., "Antisense DNA Methylphosphonate Inhibition of C–MYC Gene Expression in Transgenic Mice," *FASEB J.*, 75th Annual Meeting, Atlanta, GA, 1991, Part 2, Abstract No. 6218.
Sell et al., "Simian virus 40 large tumor antigen is unable to transform mouse embryonic fibroblasts lacking type 1 insulin–like growth factor receptor", *Proc. Natl. Acad. Sci. USA*, 1993, 90, 11217–11221.
Sell et al., "Effect of a Null Mutationof the Insulin–Like Growth Factor I Receptor Gene on Growth and Transformation of Mouse Embryo Fibroblasts", *Mol. Cell. Biol.*, 1994, 14, 3604–3612.

(List continued on next page.)

*Primary Examiner*—Scott D. Priebe
*Assistant Examiner*—Anne Marie S. Beckerleg
(74) *Attorney, Agent, or Firm*—Woodcock Washburn Kurtz Mackiewicz & Norris LLP

(57) ABSTRACT

A method of inducing resistance to tumor growth comprising placing tumor cells in culture in vitro supplemented with a pro-apoptotic agent for a period of time, transferring the tumor cells into a diffusion chamber, thereby producing a cell-containing chamber, inserting the chamber into a mammal for a therapeutically effective time, thereby inducing resistance to tumor growth. The pro-apoptotic agents include nucleic acid molecules, proteins or peptides, non-proteins or non-polynucleotide compounds, and a physical conditions.

19 Claims, 10 Drawing Sheets

OTHER PUBLICATIONS

Valentinis et al., "The role of the insulin–like growth factor I receptor in the transformation by simian virus 40 T antigen", *Oncogene,* 1994, 9, 825–831.

Coppola et al., "A Functional Insulin–Like Growth Factor I Receptor is Required for the Mitogenic and Transforming Activities of the Epidermal Growth Factor Receptor", *Mol. Cell. Biol.,* 1994, 14, 4588–4595.

Resnicoff et al., "Rat Glioblastoma Cells Expressing an Antisense RNA to the Insulin–like Growth Factor–1 (IGF–1) Receptor are Nontumorigenic and Induce Regression o Wild–Type Tumors", *Cancer Res.,* 1994, 54, 2218–2222.

Resnicoff, M., et al., "Growth Inhibition of Human Melanoma Cells in Nude Mice by Antisense Strategies to the Type 1 Insulin–like Growth Factor Receptor", *Cancer Res.,* 1994, 54, 4848–4850.

Harrington et al., "c–Myc–induced apoptosis in fibroblasts is inhibited by specific cytokines", *EMBO J.,* 1994, 13, 3286–3295.

Goldring and Goldring, "Cytokines and Cell Growth Control", *Crit. Rev. Eukaryot. Gene Expr.,* 1991, 1, 301–326.

Baserga and Rubin, "Cell Cycle and Growth Control", *Crit. Rev. Eukaryot. Gene Expr.,* 1993, 3, 47–61.

Pietrzkowski et al., "Constitutive Expression of Insulin–like Growth Factor 1 and Insulin–like Growth Factor 1 Receptro Abrogates All Requirements for Exogenous Factors", *Cell Growth & Diff,* 1992, 3, 199–205.

Pietrzkowski et al., "Roles of Insulinlike Growth Factor 1 (IGF–1) and the IGF–1 Receptor in Epidermal Growth Factor–Stimulated Growth of 3T3 Cells", *Mol. Cell. Biol.,* 1992, 12, 3883–3889.

Buttyan, R., et al., "Induction of the TRPM–2 Gene in Cells Undergoing Programmed Death", *Mol. Cell Biol.,* 1989, 9, 3473–3481.

Kaufmann, S.H., "Induction of Endonucleolytic DNA Cleavage in Human Acute Myelogenous Leukemia Cells by Etoposide, Camptothecin, and Other Cytotoxic Anticancer Drugs: A Cautionary Note", *Cancer Res.,* 1989, 49, 5870–5878.

Barry, M.A., et al., "Activiation of Programmed Cell Death by Cisplatin, Other Anticancer Drugs, Toxins and Byperthermia", *Biochem Pharmacol,* 1990, 40, 2353–2362.

Bursch, W., et al., "Determination of the length of the histological stages of apoptosis in normal liver and in altered hepatic foci of rats", *Carcinogenesis,* 1990, 11, 847–853.

Lange et al., "IL–4–and IL–5–Dependent Protective Immunity to *Onchocerca Volvulus* infective Larvae in BALB/cBYJ mice", *J. Immunol.,* 1994, 153, 205–211.

Lanza et al., "Xenogeneic Humoral Responses to Islets Transplated in Biohybrid Diffusion Chambers", *Transplantation,* 1994, 57, 1371–1375.

Trojan et al., "Treatment and Prevention of Rat Glioblastoma by Immunogenic C6 Cells Expressing Antisense Insulin–Like Growth Factor I RNA", *Science,* 1993, 259, 94–97.

Martin et al., "Development of an in Vitro Assay for the Survival of Cells Suspended from BA1112 Rat Sarcomas", *Eur. J. Cancer Clin. Oncol.,* 1983, 19, 791–797.

Preston et al., "Regulation of Apoptosis by Low Serum in Cells of Different Stages of Neoplastic Progression", *Cancer Res.,* 1994, 54, 4214–4223.

Brown, "Gene Therapy 'Oversold' By Researchers, Jounalists", *Washington Post,* Dec. 8, 1995, pp. 1 and A22.

Conley, "Transplantation of nervous system tumors in diffusion chambers", *J. Neurosurg.,* 1974, 41, 332–338.

Kolata, "In the rush toward gene therapy, some see a high risk of failure", *The New York Times,* Jul. 25, 1995, p. C3.

Marshall, "Gene Therapy's Growing Pains", *Science,* 1995, 269, 1050–1055.

Miller et al., "Gene Transfer and Antisense Nucleic Acid Techniques", *Parasitology Today,* 1994, 10(3), 92–97.

Tseng et al., "Antisense oligonucleotide technology in the development of cancer therapeutics", *Cancer Gene Therapy,* 1994, 1(1), 65–71.

Wu–Pong, "Oligonucleotides: Opportunities for Drug Therapy and Research", *Pharm. Tech.,* 1994, 102, 104, 106, 108, 110–112, and 114.

Ray et al., "Ca2+ antagonists inhibit DNA fragmentation and toxic cell death induced by acetaminophen", *FASEB J.,* 1993, 7, 453–463.

Becker et al., "Proliferation of human malignant melanomas is inhibited by antisense oligodeoxynucleotides targeted against basic fibroblast growth factor", *EMBO J.,* 1992, 8(12), 3685–3691.

Abraham, et al., "Survival and Development of larval *Onchocerca Volvulus* in Diffusion Chambers Implanted in Primate and Rodent Hosts", *J. Parasitol.,* 1993, 79, 571–582.

Baserga, R., "Oncogenes and the Strategy of Growth Factors", *Cell,* 1994, 79, 927–930.

Scher, C.D., et al., "Platelet–Derived Growth Factor and the Regulation of the Mammalian Fibroblast Cell Cycle", *Biochem. Biophys. Acta.,* 1979, 560, 217–241.

Stiles, C.D., et al., "Dual control of cell growth by somatomedins and platelet–derived growth factor", *Proc. Natl. Acad. Sci. USA,* 1979, 76, 1279–1283.

Ullrich, A. et al., "Insulin–Like Growth Factor I Receptor Primary Structure: Comparison with Insulin Receptor Suggests Structural Determinants that Define Functional Specificity", *EMBO J.,* 1986, 5(10), 2503–2512.

Ullrich, A. And Schlessinger, J., "Signal Transduction by Receptors with Tyrosine Kinase Activity", *Cell,* 1990, 61, 203–212.

Zhou–Li, F., et al., "Association of Insulin Receptor Substrate 1 with Simian Virus 40 Large T Antigen", *Mol. Cell Biol.,* 1995, 15, 4232–4239.

Cox et al., "Identification of a Peptide Recognized by Five Melanoma–Specific Human Cytotoxic T Cell Lines", *Science,* 1994, 264, 716–719.

D'Ambrosio et al., "A Soluble Insulin–like Growth Factor I Receptor That Induces Apoptosis for Tumor Cells in vivo and Inhibits Tumorigenesis", *Cancer Res.,* 1996, 56, 4013–4020.

Kawakami et al., "Identification of a human melanoma antigen recognized by tumor–infiltrating lymphocytes associated with in vivo tumor rejection", *Proc. Natl. Acad. Sci. USA,* 1994, 91, 6458–6462.

Mandelbolm et al., "CTL Induction by a tumour–associated antigen octapeptide derived from a murine lung carcinoma", *Nature,* 1994, 369, 67–71.

Resnicoff et al., "The Insulin–like Growth Factor I Receptor Protects Tumor Cells from Apoptosis in Vivo", *Cancer Res.,* 1995, 55, 2463–2469.

Resnicoff et al., "Correlation between Apoptosis, Tumorigenesis, and Levels of Insulin–like Growth Factor I Receptors", *Cancer Res.,* 1995, 55, 3739–3741.

\* cited by examiner

```
                                -30
                                MetLysSerGlyGlyGlySerPro
TTTTTTTTTTGAGAAAGGGAATTTCATCCCAAATAAAGGAATGAAGTCTGGCTCCGGAGGAGGGTCCCCG
                                                          -1  1 ← α subunit
       -20                          -10
ThrSerLeuTrpGlyLeuPheLeuSerAlaAlaLeuSerLeuTrpProThrSerGlyValGluIleGluIleCysGlyPro
ACCTCGCTGTGGGGGCTCCTGTTTCTCTCCGCCGCGCTGTCGCTGTGGCCGACGAGTGGAGAAATCTGCGGGCCA       150
                                                                        30
GlyIleAspIleArgAsnAspTyrGlnGlnLeuLeuLysArgLeuGluAsnCysThrValIleGluGlyTyrLeuHis
GGCATCGACATCCGCAACGACTATCAGCAGCTGCTGAAGCGGCTGGAGAACTGCACGGTGATCGAGGGCTACCTCCAC
                40                                  50
IleLeuLeuIleSerLysAlaGluAspTyrArgSerTyrArgPheProLysLeuThrValIleThrGluTyrLeu
ATCCTGCTCATCTCCAAGGCCGAGGACTACCGCAGCTACCGCTTCCCCAAGCTCACGGTCATTACCGAGTACTTG      300
          60                          70                              80
LeuPheArgAlaAlaGlyAlaLeuLeuSerLeuGluAspLeuPheProAsnLeuThrValIleArgGlyTrpLys
CTGTTCCGAGCTGCTGGCGCCCTCCTGAGCCTCGAGGACCTCTTCCCCAACCTCACGGTCATCCGCGGCTGGAAA
                    90                        100
LeuPheTyrAsnTyrAlaLeuValIlePheGluMetThrAsnLeuLysAspIleGlyLeuTyrAsnLeuArgAsn
CTCTTCTACAACTACGCCCTCGTCATCTTCGAGATGACCAATCTCAAGGATATTGGGCTTTACAACCTGAGGAAC    450
      110                         120                    130
IleThrArgGlyAlaIleArgIleGluLysAsnAlaAspLeuCysTyrLeuSerThrValAspTrpSerLeuIle
ATTACTCGGGGCGCCATCAGGATTGAGAAAAATGCTGACCTGTGCTACCTCTCCACTGTGGACTGGTCCCTGATC
              140                            150
LeuAspAlaValSerAsnAsnTyrIleValGlyAsnLysProProLysGluCysGlyAspLeuCysProGlyThr
CTGGATGCGGTGTCCAATAACTACATTGTGGGGAATAAGCCCCCAAAGGAATGTGGGGACCTGTGCCCAGGGACC     600
       160                           170                             180
MetGluLysProMetCysGluLysThrThrIleAsnAsnGluTyrAsnTyrArgCysTrpThrThrAsnArg
ATGGAGAAGCCGATGTGTGAGAAGACCACCATCAACAATGAGTACAACTACCGCTGCTGGACCACAAACCGC

FIG. 4A
```

```
CysGlnLysMetCysProSerThrCysGlyLysArgAlaCysThrGluAsnAsnGluCysCysHisProGluCys
TGCCAGAAATGTGCCCAAGCACGTGTGGGAAGCGGGCGTGCACCGAGAACAATGAGTGCTGCCACCCGAGTGC      750
          190                           200
LeuGlySerCysSerAlaProAspAsnAspThrAlaCysValAlaCysArgHisTyrTyrAlaGlyValCys
CTGGGCAGCTGCAGCGCGGCCTGACAACGACACGGCCTGTGTAGCTGCCGCCACTACTATGCCGGTGTCTGT
          210                           220                           230
ValProAlaCysProProAsnThrTyrArgPheGluGlyTrpArgCysValAspArgAspPheCysAlaAsnIle
GTGCCTGCCTGCCCGCCCAACACCTACAGGTTTGAGGGCTGGCGCTGTGTGGACCGTGACTTCTGCGCCAACATC   900
          240                           250
LeuSerAlaGluSerSerAspSerGlyGluGlyPheValIleHisAspGlyGluCysMetGlnGluCysProSerGly
CTCAGCGCCGAGAGCAGCGACTCCGGAGAGGGCTTTGTGATCCACGACGGGGAGTGCATGCAGGAGTGCCCCTCGGGC
          260                           270                           280
PheIleArgAsnGlySerGlnSerMetTyrCysIleProCysGluGlyProCysProLysValCysGluGluGlu
TTCATTCGCAACGGCAGCCAGAGCATGTACTGTATCCCTTGTGAAGGTCCTTGCCCGAAGGTCTGTGAGGAAGAA    1050
          290                           300
LysLysThrLysThrIleAspSerValThrSerAlaGlnMetLeuGlnGlyCysThrIlePheLysGlyAsnLeu
AAGAAAACAAAGACCATTGATTCTGTTACTTCTGCTCAGATGCTCCAAGGATGCACCATCTTCAAGGGCAATTTG
          310                           320                           330
LeuIleAsnIleArgArgGlyAsnAsnIleAlaSerGluLeuGluAsnPheMetGlyLeuIleGluValValThr
CTCATTAACATCCGACGGGGGAATAACATTGCTTCAGAGCTGGAGAACTTCATGGGGCTCATCGAGGTGGTGACG    1200
          340                           350
GlyTyrValLysIleArgHisSerHisAlaLeuValSerLeuSerPheLeuLysAsnLeuArgLeuIleLeuGly
GGCTACGTGAAGATCCGCCATTCTCATGCCTTGGTCTCCTTGTCCTTCCTAAAAAACCTTCGCCTCATCCTAGGA
          360                           370                           380
GluGluGlnLeuGluGlyAsnTyrSerPheTyrValLeuAspAsnGlnAsnLeuGlnLeuTrpAspTrpAsp
GAGGAGCAGCTAGAAGGGAATTACTCCTTCTACGTCCTTGACAACCAGAACTTGCAGCAACTGTGGGACTGGGAC    1350
          390                           400
```

FIG. 4B

```
                                                                              430
     410                    420
HisArgAsnLeuThrIleLysAlaGlyLysMetTyrPheAlaPheAsnProLysLeuCysValSerGluIleTyr
CACCGCAACCTGACCATCAAAGCAGGGAAAATGTACTTTGCTTTCAATCCCAAATTATGTTTCGAAATTTAC 440                    450                                      1500
ArgMetGluGluValThrGlyLysGlyArgGlnSerLysGlyAspIleAsnThrArgAsnAsnGlyGluArg
CGCATGGAGGAAGTGACGGGCAAAGGCCGCCAAAGCAAGGGGACATAAACACCAGGAACAACGGGGAGAGA 470                                 480
AlaSerCysGluSerAspValLeuHisPheThrSerLysAsnArgIleIleIleThrTrpHis
GCCTCCTGTGAAAGTGACGTCCTGCATTTCACCTCGAAGAATCGCATCATCATAACCTGGCAC

1650
ArgTyrArgProProAspTyrArgAspLeuIleSerPheThrValTyrTyrLysGluAlaProPheLysAsnVal
CGGTACCGGCCCCCCGACTACAGGGATCTCATCAGCTTCACCGTTTACTACAAGGAAGCACCCTTTAAGAATGTC 510                     520                            530
ThrGluTyrAspGlyGlnAspAlaCysGlySerAsnSerTrpAsnMetValAspLeuProProAsnLys
ACAGAGTATGATGGGCAGGATGCCTGCGGCTCCAACAGCTGGAACATGGTGGACCTTCCGCCCAACAAG

1800
AspValGluProGlyIleLeuLeuHisGlyLeuLysProTrpThrGlnTyrAlaValThrValLysAlaValThr
GACGTGGAGCCCGGCATCTTACTACATGGGCTGAAGCCCTGGACTCAGTACGCCGTTTACGTCAAGGCTGTGACC 560                               580
LeuThrMetValGluAsnAsnSerAlaSerAsnSerSerGlnLeuIleValLysTrpAsnProProSer
CTCACCATGGTGGAGAACAACGACCATATCCGTGGGGCCAAGAGTGAGAATCTTGTACATCGCACCAATGCTTCAGTT

600
ProSerIleProLeuAspValLeuSerAlaSerAsnAspHisIleArgGlyAlaLysSerGluAsnLeuValLysTrpAsnProProSer
CCTTCCATTCCCTTGGACGTTCTTTCAGCATCGAACATCCTCTTCAGTTAATCGTGAAGTGGAACCCTCCCTCT 1950
                           620                    630
LeuProAsnGlyTyrAsnLeuSerTyrTyrIleValArgTrpGlnProGlnArgGlyAspGlyTyrLeuTyrArgHis
CTGCCCAACGGCAACCTGAGTTACTACATTGTGCGCTGGCAGCCCCAGCCTGGAGGACGGCTACCTTTACCGGCAC
```

FIG. 4C

```
                                                                                    650
AsnTyrCysSerLysAspLysIleProIleArgLysTyrAlaAspGlyThrIleAspIleGluValThrGlu
AATTACTGCTCCAAAGACAAATCCCATCAGGAAGTATGCCGACGGCACCATCGACATTGAGGAGGTCACAGAG   2100
           660                              670                     680
AsnProLysThrGluValCysGlyGlyGluLysGlyProCysCysAlaCysProLysThrGluAlaGluLysGln
AACCCCAAGACTGAGGTGTGTGGGGGAGAAAGGGCCTTGCTGCGCCTGCCCCAAAACTGAAGCCGAGAAGCAG   2250
                                                     700
AlaGluLysGlyGluAlaGluTyrArgLysValPheGluHisAsnSerIlePheValProArgPro
GCCGAGAAGGGAGAGGCTGAATACCGCAAAGTCTTTGAGCACAACTCCATCTTCGTGCCCAGACCT          2250
                                                  730
GluArgLysArgAspValMetGlnValAlaAlaAsnThrThrThrAlaAla
GAAAGGAAGCGGGACGTCATGCAAGTGGCCGCCAACACCACCACGGCCGCA
↑   710      β subunit        720
                                    750
AspThrTyrAsnIleThrAspProGluLeuGluTyrProPhePheGluSerArgValAspAsnLys
GACACCTACAACATCACCGACCCGGAACTGGAATACCCCTTTCTTTGAGAGCAGAGTGGATAACAAG         2400
           760                              770                     780
GluArgThrValIleSerAsnLeuArgProPheThrLeuTyrArgIleAspIleHisSerCysAsnHisGluAla
GAGAGAACTGTCATTTCAAACCTTCGGCCCTTTCACATTGTACCGCATCGATATCCACAGCTGCAACCACGAGGCT
                                                     800
GluLysLeuGlyCysSerAlaSerAsnPheValPheAlaArgThrMetProAlaGlyAlaAspIlePro
GAGAAGCTGGGCTGCAGCGCCTCCAACTTCGTCTTTGCAAGGACTATGCCCGCAGAAGGAGCAGATGACATTCCT  2550
           810                              820                     830
GlyProValThrArgProGluProArgProAsnSerIlePheLeuLysTrpProGluProAsnGly
GGGCCAGTGACCCGGGACCTGAACCTAGACCCAAGGCCTGAAAACCTCCATCTTTTAAAGTGGCCGGAACCTGAGAATCCCAATGGA
                                                     850
LeuIleLeuMetTyrGluIleLysTyrGlySerGlnValGluAspGlnArgGluCysValSerArgGlnGluTyr
TTGATTCTAATGTATGAAATAAAATACGGATCACAAGTTGAGGATCAGCGCGAGAATGTGTGTCCAGAGGAATAC   2700
```

FIG. 4D

```
                     860                                                       870                             880
ArgLysTyrGlyGlyAlaLysLeuAsnArgLeuAsnProGlyAsnTyrThrAlaArgIleGlnAlaThrSerLeu
AGGAAGTATGGAGGGGCCAAGCTAAACCGGGAACTACACGCCCGGATTCAGGCCACATCTCTC
                          890                                              900
SerGlyAsnGlySerTrpThrAspProValPhePheTyrValGlnAlaLysThrGlyTyrGluAsnPheIleHis              2850
TCTGGGAATGGGTCGTGGACAGATCCTGTTCTTCTATGTCCAGGCCAAAACAGGATATGAAAACTTCATCCAT
              910                                          920                            930
LeuIleIleAlaAlaLeuProValAlaValAlaLeuLeuIleValGlyGlyValIleMetLeuTyrValPheHisArg
CTGATCATCGCTGCCCGTCCGCTCTGTTGATCGTGGGAGGGTTGGTGATTATGCTGTACGTCTTCCATAGA
                  940                                             950
LysArgAsnAsnSerArgLeuGlyValLeuAsnGlyValLeuTyrAlaSerValAsnProGluTyrPheSerAlaAlaAsp              3000
AAGAGAAATAACAGCAGGCTGGGGGTGCTGAATGGAGTGCTGTATGCCTCTGTGAACCCGGAGTACTTCAGCGCTGCTGAT
              960                                            970                       980
ValTyrValProAspGluTrpGluValAlaArgGluLysIleThrMetSerArgGluLeuGlyGlnGlySerPhe
GTGTACGTTCCTGATGAGTGGGAGGTGGCTCGGGAGAAGATCACCATGAGCCGGGAACTTGGGCAGGGGTCGTTT
                     990                                             1000
GlyMetValTyrGluGlyValValAlaLysGlyValValLysAspGluProThrArgValAlaIleLysThrVal              3150
GGGATGGTCTATGAAGGAGTTGCCAAGGGTGTGGTGAAAGATGAACCTACGAGAGTGGCCATTAAAACAGTG
                    1010                                             1020                     1030
AsnGluAlaAlaSerMetArgGluMetArgIleGluPheLeuAsnGluAlaSerValMetLysGluAsnCysHis
AACGAGGCCGCAAGCATGCGTGAGATGAGGATTGAGTTTCTCAACGAAGCTTCTGTGATGAAGGAGTTCAATTGTCAC
                1040                                          1050
HisValValArgLeuLeuGlyValValSerGlnGlyGlnProThrLeuValIleMetGluLeuMetThrArgGly              3300
CATGTGGTGCGATTGCTGGGTGTGGTGTCCCAAGGCCAACACTGGTCATCATGGAACTGATGACACGGGGC
                 1060                                            1070                  1080
AspLeuLysSerTyrLeuArgSerLeuArgProGluMetGluAsnProValLeuAlaProProSerLeuSer
GATCTCAAAAGTTATCTCCGGTCTCTGAGGCCAGAAATGGAGAATCCAGTCCTAGCCACCTCCAAGCCTGAGC

FIG. 4E
```

```
                    1090                                          1100
LysMetIleGlnMetAlaGlyGluIleAlaAspGlyMetAlaTyrLeuAsnAlaAsnLysPheValHisArgAsp
AAGATGATTCAGATGGCCGGAGAGATTGCAGACGGCATGGCATACCTCAACGCCAATAAGTTCGTCCACAGAGAC  3450
   1110                                           1130
LeuAlaAlaArgAsnCysMetValAlaGluAspPheThrValLysIleGlyAspPheGlyMetThrArgAspIle
CTTGCCGCCCGGAATTGCATGGTAGCCGAAGATTTCACAGTCAAAATCGGAGATTTTGGTATGACGCGAGATATC
                  1140                                    1150
TyrGluThrAspTyrTyrArgLysGlyGlyLysGlyLeuLeuProValArgTrpMetSerProGluSerLeuLys
TATGAGACAGACTATTACCGGAAAGGAGGGCTGCTGCCCGTGCGCTGGATGTCTCCTGAGTCCCTCAAG  3600
                                          1180
AspGlyValPheThrThrTyrSerAspValTrpSerPheGlyValValLeuTrpGluIleAlaThrLeuAlaGlu
GATGGAGTCTTCACCACTTACTCGGACGTCTGGTCCTTCGGGGTCGTCCTGTGGGAGATCGCCACACTGGCCGAG
              1190                                   1200
GlnProTyrGlnGlyLeuSerAsnGluGlnValLeuArgPheValMetGluGlyGlyLeuLeuAspLysProAsp
CAGCCCTACCAGGGCTTGTCCAACGAGCAAGTCCTTCGCTTCGTCATGGAGGGCGGCCTTCTGGACAAGCCAGAC  3750
                                    1230
AsnCysProAspMetLeuPheGluLeuMetArgMetCysTrpGlnTyrAsnProLysMetArgProSerPheLeu
AACTGTCCTGACATGCTGTTTGAACTGATGCGCATGTGCTGGCAGTATAACCCCAAGATGAGGCCTTCCTTCCTG
                1240                                    1250
GluIleIleSerSerIleLysGluGluMetGluProGlyPheArgGluValSerPheTyrTyrSerGluAsn
GAGATCATCAGCAGCATCAAAGAGGAGATGGAGCCTGGCTTCCGGGAGGTCTCCTTCTACTACAGCGAGGAGAAC  3900
                                     1280
LysLeuProGluGluProGluLeuGluLeuAspLeuGluProGluAsnMetGluSerValProLeuAspProSerAlaSer
AAGCTGCCGGAGGAGCCGGAGCTGGAGCTGGACCTGGAGCCCGAGAACATGGAGAGCGTCCCCCTGGACCCCTCGGCCTCC
           1290                                 1300
SerSerLeuProAspArgHisSerGlyHisLysAlaGluAsnGlyProGlyValLeuVal
TCGTCCTCCCTGCCACTGCCCGACAGACACTCAGGACACAAGGCCGAGAACGGGCCCGGGGGTGCTGGTC  4050
```

FIG. 4F

```
                              1310                                    1320                                         1330
LeuArgAlaSerPheAspGluArgGlnProTyrAlaHisMetAsnGlyGlyArgLysAsnGluArgAlaLeuPro
CTCCGCGCGGCCAGCTTCGACGAGAGACAGCCTTACGCCCACATGAACGGGGGCCGCAAGAACGAGCGGGCCTTGCCG

LeuProGlnSerSerThrCysEnd
CTGCCCCAGTCTTCGACCTGCTGATCCTTGGATCCTGAATCTGTGCAAACAGTAACGTGTGCGCACGCGCAGCGG          4200
GGTGGGGGGAGAGAGAGTTTTAACAATCCATTCACAGCCTCCTGTACTTCAGTGGATCTTCAGTTCTGCCCT
TGCTGCCCGGGAGACAGCTTCTCTGCAGTAAAAACACATTTGGGATGTTCCTTTTTCAATATGCAAGCAGCTT          4350
TTTATTCCCTGCCCAAACCCTTAACTGACATGGGCCTTTAAGAACCTTCCCTGTCCCTGTCCTTCTCTGCTTCATAAC       4500
ACTTGAGAACCAGTCTCCTCACTCTGTCCCTGTCCTTCTCCCTGTTCTCCCTTTCTCTGTTGAGGAAGTGGCTGTCCCTGTGGCCCC
GGAAAAATAATTGCCACAAGTCCAGTGGGTCATTACAAAAAAAACACGTGGAGATGGAAATTTTACCT              4650
ATCCAACCACTGTACACACCCGCCTGACACCATGAAATTTACAAGGGCCATCGTTCATCCAAGGCTGTTACCATTTTAACGC
TTATCTTTCACCTTTCTAGGGACATGAAATTTACAAGGGCCATCGTTCATCCAAGGCTGTTACCATTTTAACGC
TGCCTAATTTTGCCAAATCCTGAACTTTCTCCCTCATCGGCCCTGATTCCTGTCCGTGTCCGAGGCATGGG           4800
TGAGCATGGCAGCTGGTTGCTTCATTTGAGAGACACACTCCGTCCGACACACTCCGTCCATCCGACTCCTGCTGT
GCTGCTCAAGGCCACAGGCACACAGGTCTCATTGCTTCTGACTAGATTATTATTTGGGGAACTGGACACAATAG          4950
GTCTTTCTCAGTGAAGGTGGGGAGAAGCTGAACCGGC                                           4989
```

METHOD OF INDUCING RESISTANCE TO TUMOR GROWTH

CROSS REFERENCE TO RELATED APPLICATIONS

The present application is a continuation in part of U.S. Ser. No. 08/340,732 filed Nov. 16, 1994, U.S. Pat. No. 5,714,170, and international application Serial No. PCT/US95/14952 filed Nov. 15, 1995, both of which are incorporated herein by reference.

REFERENCE TO GOVERNMENT GRANTS

This invention was funded by National Institute of Health Grants GM 33694 and CA 56309. The U.S. government may have certain rights in the invention.

FIELD OF THE INVENTION

The present application is directed to inducing resistance to tumor growth by using diffusion chambers implanted in mammals.

BACKGROUND OF THE INVENTION

Traditional methods of treating tumors in mammals include procedures such as, for example, surgical removal of the tumor, injection or implantation of toxic treatments or syngeneic tissue samples, chemotherapy, and irradiation. The ultimate goal of each of these procedures is to reduce the growth of existing tumors, preferably abrogating tumor growth to the point of complete regression, and/or to induce resistance to future tumor growth. These procedures have numerous effects on tumor cells.

Tumors and other neoplastic tissues are known to undergo apoptosis spontaneously or in response to treatment. Examples include several types of leukemia, non-Hodgkin's lymphoma, prostate tumor, pancreatic cancer, basal and squamous cell carcinoma, mammary tumor, breast cancer, and fat pad sarcoma. Several anticancer drugs have been shown to induce apoptosis in target cells. Buttyan, et al., *Mol. Cell. Biol.*, 1989, 9, 3473–3481; Kaufmann, *Cancer Res.*, 1989, 49, 5870–5878; and Barry, et al., *Biochem. Pharmacol.*, 1990, 40, 2353–2362, all of which are incorporated herein by reference. Certain mildly adverse conditions can result in the injured cell dying by programmed cell death, including hyperthermia, hypothermia, ischemia, and exposure to irradiation, toxins, and chemicals. It should be noted that many of these treatments will also result in necrosis at higher doses, suggesting that mild injury to a cell might induce cell suicide, perhaps to prevent the inheritance of a mutation, while exposure to severe conditions leads directly to cell death by necrosis. However, the death process is difficult to observe due to the rapidity of the process and the reduced amount of inflammation. For these reasons, quantification of apoptosis is often difficult. A method of measuring the duration of the histologically visible stages of apoptosis (3 hours in normal rat liver) and a formula by which to calculate the cell loss rate by apoptosis is set forth by Bursch, et al., *Carcinogenesis*, 1990, 11, 847–853.

Evidence is also rapidly accumulating that growth factors and their receptors play a crucial role in the establishment and maintenance of transformed phenotypes. It is well established that growth factors play a crucial role in the establishment and maintenance of the transformed phenotype. Mouse embryo cells with a targeted disruption of the type 1 insulin-like growth factor receptor (IGF-IR) genes cannot be transformed by SV40 T antigen and/or an activated Ha-ras oncogene that easily transform embryo cells generated from their wild-type littermates. Sell, et al., *Proc. Natl. Acad. Sci. USA*, 1993, 90, 11217–11221; Sell, et al., *Mol. Cell. Biol.*, 1994, 14, 3604–3612; Valentinis, et al., *Oncogene*, 1994, 9, 825–831; and Coppola, et al., *Mol. Cell. Biol.*, 1994, 14, 4588–4595. Expression of an antisense RNA to the IGF-IR RNA in C6 rat glioblastoma cells not only abrogates tumorigenesis in syngeneic rats, but also causes complete regression of established wild type tumors. Resnicoff, et al., *Cancer Res.*, 1994a, 54, 2218–2222 and Resnicoff, et al., *Cancer Res.*, 1994b, 54, 4848–4850. Related to this finding is also the report by Harrington, et al. (*EMBO J.*, 1994, 13, 3286–3295), that IGF-I (and PDGF) protect cells from c-myc induced apoptosis. A decrease in cell death rate in tumors could certainly be an important mechanism for tumor growth. Baserga, *The Biology of Cell Reproduction*, Harvard University Press, Cambridge, Mass., 1985. Cells expressing an antisense RNA to the IGF-IR RNA or cells pre-incubated with antisense oligodeoxynucleotides to the IGF-IR RNA completely lose their tumorigenicity when injected in either syngeneic or nude mice. Resnicoff et al., 1994a, 1994b. The injected cells were suspected of undergoing apoptosis or, at any rate, some form of cell death. Dying cells, however, are very difficult to demonstrate, because dying cells, especially in vivo, disappear very rapidly, and one is left with nothing to examine.

The importance of the IGF-I receptor in the control of cell proliferation is also supported by considerable evidence: 1) many cell types in culture are stimulated to grow by IGF-I (Goldring, et al., *Crit. Rev. Eukaryot. Gene Expr.*, 1991, 1, 301–326 and Baserga, et al., *Crit. Rev. Eukaryot. Gene Expr.*, 1993, 3, 47–61), and these cell types include human diploid fibroblasts, epithelial cells, smooth muscle cells, T lymphocytes, myeloid cells, chondrocytes, osteoblasts as well as the stem cells of the bone marrow; 2) interference with the function of the IGF-I receptor leads to inhibition of cell growth. This has been demonstrated by using antisense expression vectors or antisense oligodeoxynucleotides to the IGF-I receptor RNA: the antisense strategy was successful in inhibiting cellular proliferation in several normal cell types and in human tumor cell lines (Baserga, et al., 1994, supra.); and 3) growth can also be inhibited using peptide analogues of IGF-I (Pietrzkowski, et al., *Cell Growth & Diff.*, 1992a, 3, 199–205 and Pietrzkowski, et al., *Mol. Cell. Biol.*, 1992b, 12, 3883–3889), or a vector expressing an antisense RNA to the IGF-I RNA (Trojan, et al., 1993, supra.). The IGF autocrine or paracrine loop is also involved in the growth promoting effect of other growth factors, hormones (for instance, growth hormone and estrogens), and oncogenes like SV40 T antigen and c-myb, and in tumor suppression, as in the case of WT1. Baserga, et al., 1994, supra.

Testing agents such as, for example, growth factors and growth factor receptors for their ability to maintain or suppress transformed phenotypes remains difficult. In order to obtain an accurate account of the tumor suppressive ability, testing should be performed in vivo. Therapies such as direct injection or implantation of toxic treatments, tissue samples, and chemotherapy often jeopardizes the overall health of the patient. However, the present invention provides a method of inducing resistance to tumor growth with markedly reduced side effects to the patient.

SUMMARY OF THE INVENTION

The present invention is directed to a method of inducing resistance to tumor growth in a mammal comprising pretreating tumor cells in vitro with a pro-apoptotic agent, placing the pretreated tumor cells in a diffusion chamber thereby producing a tumor cell-containing diffusion chamber, and inserting the tumor cell-containing diffusion chamber into the mammal for a therapeutically effective time thereby inducing resistance to tumor growth.

The present invention is also related to a method of screening test compounds for anti-cancer activity in a mammal comprising providing an in vitro tumor cell culture supplemented with a test compound, placing the tumor cells into a diffusion chamber thereby producing a tumor cell-containing diffusion chamber, inserting the tumor cell-containing diffusion chamber into the mammal for a period of time, and removing the tumor cell-containing diffusion chamber and evaluating the anti-cancer effects of the test compound.

BRIEF DESCRIPTION OF THE FIGURES

FIGS. 4A–4G provide the amino acid (SEQ ID NO:18) and nucleotide (SEQ ID NO:17) sequence of IGF-1 receptor.

DETAILED DESCRIPTION OF THE INVENTION

Figure 1:
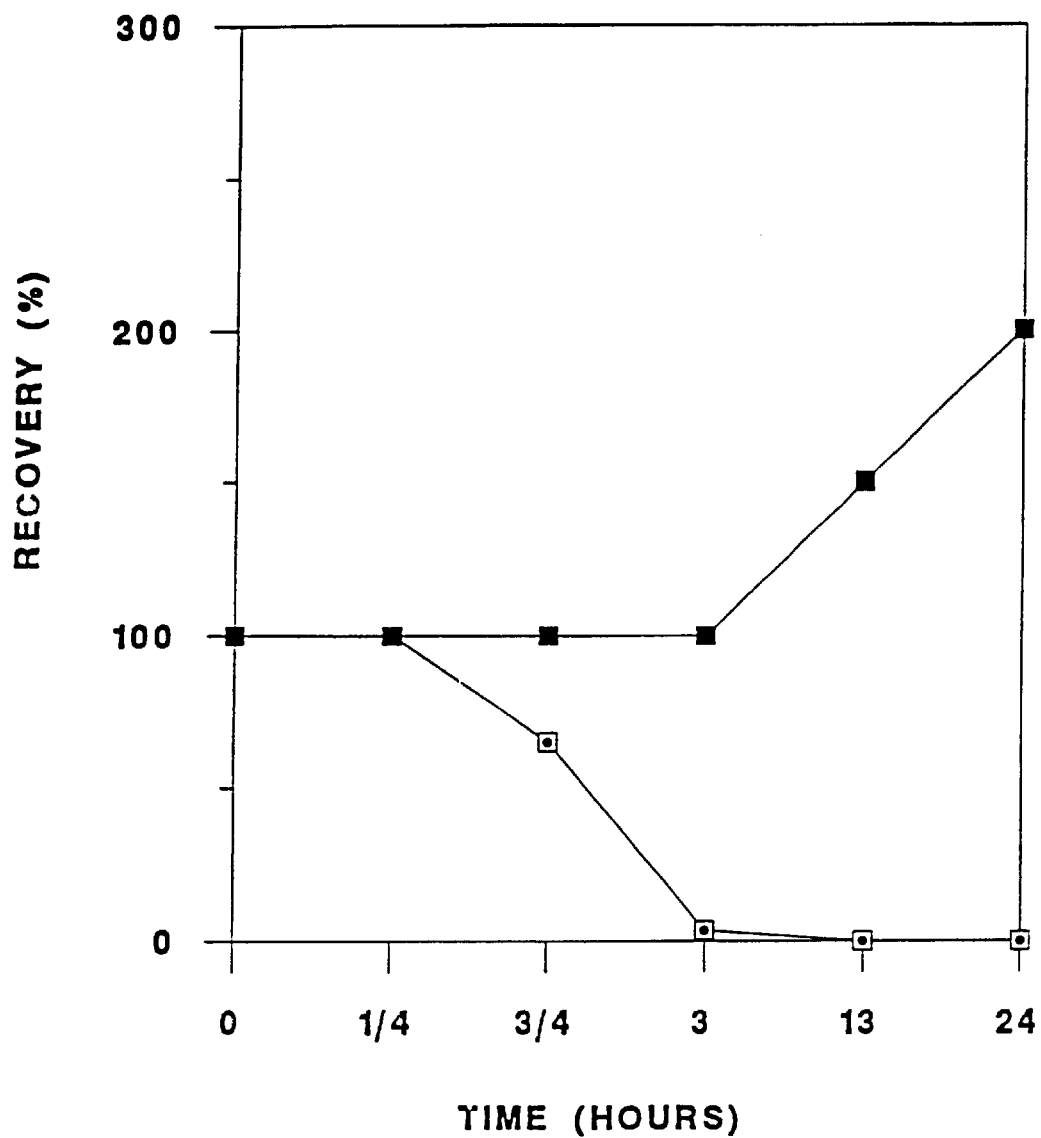
FIG. 1 is a graph representing the survival of C6 rat glioblastoma cells in diffusion chambers. Three cell lines were used: wild type C6 cells, and C6 cells stably transfected with either a sense or an antisense RNA to the IGF-I receptor RNA (Resnicoff, et al. 1994a and 1994b, both of which are incorporated herein by reference). $5 \times 10^5$ cells were inoculated in each chamber and the number of cells recovered was determined at the intervals indicated on the abscissa. Closed squares: wild type or sense cells (these curves were superimposable); open squares: antisense cells. The recovery is expressed as percentage of cells inoculated.

The present invention is directed to a method of inducing resistance to tumor growth in a mammal comprising pretreating tumor cells in vitro with a pro-apoptotic agent., placing the pretreated tumor cells in a diffusion chamber thereby producing a tumor cell-containing diffusion chamber, and inserting the tumor cell-containing diffusion chamber into the mammal for a therapeutically effective time thereby inducing resistance to tumor growth. Mammals subsequently challenged with wild-type tumor cells are resistant to the tumor cells. In addition, regression of already established tumors is evidenced.

The phrase "tumor cells," "tumors," and "cancer cells" are used interchangeably throughout the present application and include, but are not limited to, autografts, allografts, syngeneic, non-syngeneic and xenografts. Tumor cells used in the methods of the present invention can be cultured in vitro in a medium supplemented with a pro-apoptotic agent and subsequently transferred to a diffusion chamber. Tumor cells include any type of cell which upon apoptosis induces resistance to tumor growth, including and not limited to tumor cells. Preferably, treated tumor cells are placed in a diffusion chamber which is implanted in a mammal, wherein the tumor cells may preferably be the same type of tumor to which resistance is induced. However, an embodiment of the present invention includes tumors cultured in a diffusion chamber which are of a different type than the tumor to which resistance is granted. In addition, any type of tumor or cancer cell which undergoes apoptosis and induces resistance to tumor growth is useful in the present invention. Tumors which are treatable with the methods of the present invention may be primary or secondary, benign, malignant, metastatic, or micrometastatic tumors. Tumors treatable with the methods of the present invention include, but are not limited to, melanoma, prostate, ovary, mammary, pancreatic, lungs, colon, and smooth muscle tumors, as well as cells from glioblastoma, bone marrow stem cells, hematopoietic cells, osteoblasts, epithelial cells, fibroblasts, as well as any other tumor cells which undergo apoptosis and induce resistance to tumor cells.

For purposes of the present invention, mammals include and are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

The pro-apoptotic agents used in the methods of the present invention induce cell death, or apoptosis, of the tumor cells in the diffusion chamber in vivo. Apoptosis, for purposes of the present invention, is defined as cell death and includes, but is not limited to, regression of primary and metastatic tumors. Apoptosis is a programmed cell death which is a widespread phenomenon that plays a crucial role in the myriad of physiological and pathological processes. There exists a homeostatic control of cell number thought to result from the dynamic balance between cell proliferation and cell death. Necrosis is an accidental cell death which is the cell's response to a variety of harmful conditions and toxic substances. Apoptosis, morphologically distinct from necrosis, is a spontaneous form of cell death that occurs in many different tissues under various conditions. This type of cell death typically occurs in scattered cells and progresses so rapidly it is difficult to observe.

The cell death process of apoptosis occurs in two stages. The cell undergoes nuclear and cytoplasmic condensation, eventually breaking into a number of membrane-bound fragments containing structurally intact apoptotic bodies, which are phagocytosed by neighboring cells and rapidly degraded. Apoptosis is observed in many different tissues, healthy and neoplastic, adult and embryonic. Death occurs spontaneously, or is induced by physiological or noxious agents. Apoptosis is a basic physiological process that plays a major role in the regulation of cell populations.

Pro-apoptotic agents which supplement the culture medium of the tumor cells in vitro are preferably agents which induce cell death in vivo. A pro-apoptotic agent, for purposes of the present invention, is an agent which causes death of the tumor cells in the diffusion chamber in vivo such that the cell death has a tumor growth inhibiting effect, i.e., a resistant effect, on a tumor or tumors in the mammal in which the diffusion chamber is inserted. Such pro-apoptotic agents include, but are not limited to, nucleic acid molecules, proteins or peptides, non-protein or non-polynucleotide compounds, and physical conditions.

Pro-apoptotic agents, or apoptosis-inducing agents, which induce apoptosis of tumor cells in vivo include, for example, nucleic acid molecules. In one embodiment of the invention, the nucleic acid molecule is an oligonucleotide directed against DNA or RNA of a growth factor or growth factor receptor, such as, for example, insulin growth factor-1 receptor (IGF-IR). Most preferably, the oligonucleotide is directed against DNA or RNA of IGF-IR. The oligonucleotide can be directed to any portion of IGF-IR DNA or RNA. Preferably, the nucleotide sequence of the oligonucleotide includes, but is not limited to, nucleotide sequences complementary to codons 1–309 shown in FIGS. 4A–4G (SEQ ID NO: 1), comprising either RNA or DNA. The antisense oligonucleotides may also comprise nucleotide sequences complementary to portions of codons 1–309. In addition, mismatches within the nucleotide sequence of the oligonucleotide complementary to codons 1 to 309 are also within the scope of the invention. An oligonucleotide complementary to nucleotides −29 to −24 of the IGF-IR signal sequence (SEQ ID NO: 2) comprising DNA or RNA is also within the scope of the present invention. The signal sequence of IGF-IR is a 30 amino acid sequence. Contemplated by this definition are fragments of oligonucleotides within the 30 amino acid signal sequence. Alternatively, fragments of oligos within SEQ ID NO: 2 are also contemplated. Additional oligonucleotides of the invention include, but are not limited to, oligonucleotides comprising the following nucleotide sequences: GGACCCTCCTCCGGAGCC (SEQ ID NO: 3), CCGGAGCCAGACTTCAT (SEQ ID NO: 4), CTGCTCCTCCTCTAGGATGA (SEQ ID NO: 5), CCCTC-CTCCGGAGCC (SEQ ID NO: 6), TACTTCAGACCGAG-GCC (SEQ ID NO: 7), CCGAGGCCTCCTCCCAGG (SEQ ID NO: 8), and TCCTCCGGAGCCAGACTT (SEQ ID NO: 9).

In another preferred embodiment of the invention, the nucleic acid molecule is a vector which produces an oligonucleotide directed against DNA or RNA of a growth factor or growth factor receptor such as, for example, SEQ ID Numbers 1–9. The nucleic acid molecule complementary to a portion of IGF-IR RNA or DNA is inserted into an appropriate delivery vehicle, such as, for example, an expression plasmid, cosmid, YAC vector, and the like. Almost any delivery vehicle can be used for introducing nucleic acids into tumor cells. Recombinant nucleic acid molecules (or recombinant vectors) include, for example, plasmid DNA vectors, cDNA-containing liposomes, artificial viruses, nanoparticles, and the like. It is also contemplated that vectors expressing the oligonucleotides can be injected directly into the tumor cells.

The regulatory elements of the recombinant nucleic acid molecules of the invention are capable of directing expression in mammalian tumor cells, preferably human tumor cells. The regulatory elements include a promoter and a polyadenylation signal. In addition, other elements, such as a Kozak region, may also be included in the recombinant nucleic acid molecule. Examples of polyadenylation signals useful to practice the present invention include, but are not limited to, SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, can be used.

The promoters useful in constructing the recombinant nucleic acid molecules of the invention may be constitutive or inducible. A constitutive promoter is expressed under all conditions of cell growth. Exemplary constitutive promoters include the promoters for the following genes: hypoxanthine phosphoribosyl transferase (HPRT), adenosine deaminase, pyruvate kinase, β-actin, human myosin, human hemoglobin, human muscle creatine, and others. In addition, many viral promoters function constitutively in eukaryotic cells, and include, but are not limited to, the early and late promoters of SV40, the Mouse Mammary Tumor Virus (MMTV) promoter, the long terminal repeats (LTRs) of Maloney leukemia virus, Human Immunodeficiency Virus (HIV), Cytomegalovirus (CMV) immediate early promoter, Epstein Barr Virus (EBV), Rous Sarcoma Virus (RSV), and other retroviruses, and the thymidine kinase promoter of herpes simplex virus. Other promoters are known to those of ordinary skill in the art.

Inducible promoters are expressed in the presence of an inducing agent. For example, the metallothionein promoter is induced to promote (increase) transcription in the presence of certain metal ions, and the Drosophila HSP70 promoter. Other inducible promoters are known to those of ordinary skill in the art.

Recombinant nucleic acid molecules comprising oligonucleotides of the invention can be introduced into a tumor cell or "contacted" by a tumor cell by, for example, transfection or transduction procedures. Transfection refers to the acquisition by a cell of new genetic material by incorporation of added nucleic acid molecules. Transfection can occur by physical or chemical methods. Many transfection techniques are known to those of ordinary skill in the art including: calcium phosphate DNA co-precipitation; DEAE-dextran DNA transfection; electroporation; naked plasmid adsorption, and cationic liposome-mediated transfection. Transduction refers to the process of transferring nucleic acid into a cell using a DNAk or RNA virus. Suitable viral vectors for use as transducing agents include, but are not limited to, retroviral vectors, adeno associated viral vectors, vaccinia viruses, and Semliki Forest virus vectors.

In a preferred embodiment of the invention, recombinant vectors comprising oligonucleotides directed to DNA or RNA of IGF-IR, which are described, for example, in Resnicoff, et al. (1994a, 1994b, supra), both of which are incorporated herein by reference, are used. Briefly, plasmid HSP/IGF-1R AS expresses an antisense transcript 309 bp in length directed to IGF-IR RNA, under the control of a Drosophila HSP70 promoter. The hepatitis B polyadenylation signal sequence and a neomycin-resistance gene under the control of the SV40 promoter are present at the 3' termini of the 309 bp IGF-IR fragment. One skilled in the art can readily prepare additional vectors producing any of the oligonucleotides of the invention.

In other embodiments of the invention, the pro-apoptotic agents comprise proteins or peptides such as, for example, associated dominant negative mutants of IGF-IR and MHC class I peptides. Dominant negative mutants of IGF-IR 20 include, for example, soluble IGF-IR, described in D'Ambrosio, et al., *Cancer Res.*, 1996, 56, 4013–4020, incorporated herein by reference, and myristylated C-terminus of IGF-IR (MyCF). MHC class I associated peptides include, for example, Tyr-Leu-Glu-Pro-Gly-Pro-Val-Thr-Ala (SEQ ID NO: 10) recognized by melanoma-specific CTL lines (Cox, et al., *Science*, 1994, 264, 716–719), Leu-Leu-Asp-Gly-Thr-Ala-Thr-Leu-Arg-Leu (SEQ ID NO: 11) derived from gp100 and involved in regression of human melanoma (Kawakami, et al., *Proc. Natl. Acad. Sci. USA*, 1994, 91, 6458–6462), and Phe-Glu-Cys-Asn-Thr-Ala-Gln-Pro-Gly (SEQ ID NO: 12) derived from connexin 37 and induces CTL responses against murine lung carcinoma (Mandelbolm, et al., *Nature*, 1994, 369, 67–71). In addition, inverted D-amino acid anologs of the above-identified peptides, such as Ala-Thr-Val-Pro-Gly-Pro-Glu-Leu-Tyr (SEQ ID NO: 13) and Leu-Arg-Leu-Thr-Ala-Thr-Gly-Asp-Leu-Leu (SEQ ID NO: 14), are also active. Amino acid substitutions are also contemplated by the present invention. The peptides of the present invention can be made synthetically as is well known to those skilled in the art.

In other embodiments of the invention, the pro-apoptotic agents comprise non-protein or non-polynucleotide compounds such as, for example, chemotherapeutic compounds or synthetic chemical compounds. Preferably, chemotherapeutic compounds include, for example, etoposide, cisplatin, camptothecin, and tumor necrosis factor alpha (TNF-α).

In other embodiments of the invention, the pro-apoptotic agents comprise physical conditions such as, for example, hyperthermia, hypothermia, ischemia, and ionizing irradiation. In embodiments where the tumor cells are exposed to such conditions, the condition is defined for purposes of the present invention as an agent, an apoptosis-inducing agent.

Therapeutically effective doses of the pro-apoptotic agents or apoptotic-inducing agents will be about that of the drugs alone; dosages will be set with regard to weight, and clinical condition of the patient. The proportional ratio of active ingredient to culture medium will naturally depend on the chemical nature, solubility, and stability of the compounds, as well as the dosage contemplated. The culture medium is also pharmaceutically acceptable. The apoptosis-inducing agents of the invention can be used alone or in combination with other apoptosis-inducing agents.

The present invention authenticates the importance of agents, such as IGF-IR, in the growth of tumor cells, and establishes: 1) a decrease in the number of IGF-IRs, brought about by antisense strategies, causes massive cell death in vivo. This is true of several cell lines, including a human melanoma cell line; 2) the mechanism of cell death is apoptosis; 3) a decrease in the number of receptors has an inhibitory effect on growth in vitro, but is much more effective in vivo, because of the massive cell death. IGF-IR protects tumor cells against cell death in vivo.

Tumorous tissue may be excised from the mammal or patient in which the diffusion chamber will be inserted or from another source which has been cultured in vitro. The tumor cells are cultured in vitro and are supplemented with a pro-apoptotic agent such as, for example, an antisense sequence for a cell growth factor or cell growth factor receptor, for a period of time, preferably 3 to 48 hours, more preferably 24 hours. Prior to culture in vitro, the tumor cells may be gently dissociated with trypsin. The tumor cells are washed and placed in a diffusion chamber which is then implanted into a mammal or patient for a therapeutically effective amount of time such that apoptosis of the tumor cells is induced in vivo, thereby inducing resistance to tumor growth.

One important advantage of the present invention is that toxic treatments to the tumor cells such as, for example, treatment with irradiation or chemotherapeutic compounds, are performed in vitro thereby eliminating toxicity to the host mammal. In addition, tumor cells may be placed into culture in a diffusion chamber and the chamber directly implanted into a mammal, thus eliminating the possibility of physical spreading of the tumor cells which may be associated with direct injection of tumor cells into a mammal.

The present invention employs the use of a diffusion chamber, in which the cells are contained. Cells are impermeable to a filter fitted on the diffusion chamber; they cannot leave or enter the chamber. The filter on the diffusion chamber has pores in the size range of about 0.25 μm or smaller, preferably about 0.1 μm in diameter. Lange, et al., *J. Immunol.*, 1994, 153, 205–211 and Lanza, et al., *Transplantation*, 1994, 57, 1371–1375, both of which are incorporated herein by reference in their entirety. Accordingly, cell death or apoptosis, can be quantitatively determined. The use of a diffusion chamber can be extended to other cell lines, even non-syngeneic, and even from different species, because of the rapidity with which cell death occurs, about 24 hours, well before any immune reaction could be established. Indeed, 3 types of cells with an intact number of IGF-IRs (human melanoma, rat rhabdomyosarcoma and murine p6 cells), double in number in 24 hours, regardless of whether they are syngeneic or not, while cells with decreased number of IGF-IRs, die. The diffusion chambers may be useful to study other types of cell death, induced by a variety of agents, as shown in the present invention by the massive apoptosis induced by etoposide on wild type C6 cells in vivo.

Diffusion chambers useful in the present invention include any chamber which does not allow passage of cells between the chamber and the mammal in which it is implanted, however, permits interchange and passage of factors between the chamber and the mammal. The chamber may allow for multiple and sequential sampling of the contents, without contamination and without sacrificing the mammal, therefore significantly reducing the number of implantation procedures performed on the mammal.

Figure 3:
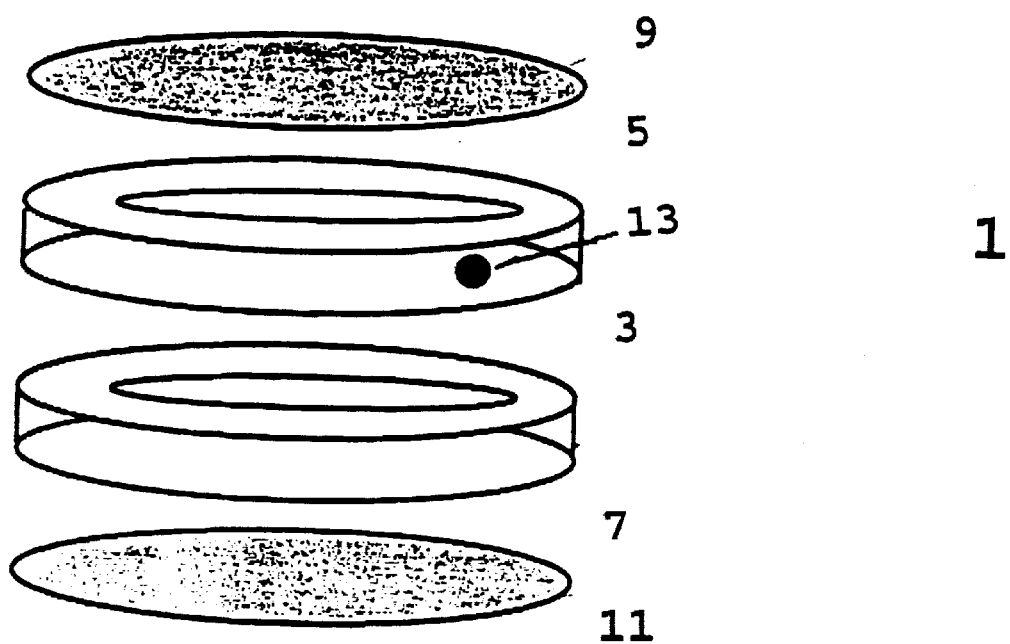
FIG. 3 shows a schematic illustration of a diffusion chamber.

Referring to FIG. 3, the diffusion chamber (1) may have a chamber barrel (3) having two ends, a first end (5) and a second end (7). The barrel may be comprised of one or more rings secured together by non-toxic means. The chamber is fitted at each end with a filter, a first filter (9) and a second filter (11). The filters are porous to factors such that the factors may pass between the chamber and the mammal. The filter pores size may be about 0.25 μm or smaller, preferably about 0.1 μm. The filters may be made of plastic, teflon, polyester, or any inert material which is strong, flexible and able to withstand chemical treatments. The filters may be secured in position with rubber gaskets which may also provide a tighter seal. On the barrel portion of the chamber, an opening (13) is provided which may be covered by a cap which is accessed from outside of the mammal's body once the chamber is implanted, thus allowing the diffusion chamber to be refilled. The cap may be screw on type of self sealing rubber and fitted to the opening. Sampling of the chamber contents may thus be performed by accessing the opening by removing the cap on the outside of the mammal's body and inserting an ordinary needle and syringe. The chamber may be made of any substance, such as and not limited to plastic, teflon, lucite, titanium, or any inert material, which is non-toxic to, and well tolerated by, mammals. In addition, the chambers should be able to survive sterilization.

The chamber may be implanted in the following non-limiting ways: subcutaneously or intraperitoneally, for example. The chamber may be removed about 24 to about 30 hours after implantation. Alternatively, a refillable chamber may be employed such that the chamber may be re-used for treatments and emptied following treatments.

Another embodiment of the present invention provides an in vivo method of screening agents for tumor resistance-inducing activity or anti-cancer therapeutic activity such as, for example, apoptosis activity. Tumor cells in media are cultured in the presence of a test compound. Contacting of cells with the test compound may be by direct delivery to the tumor cells in vitro or the test compound may be delivered to the test animal as a pharmaceutical formulation. After culture for about 24 hours in vitro, the tumor cells are washed with phosphate buffered saline and transferred to the diffusion chamber, which is subsequently implanted into a test animal, such as a rat or mouse, or other suitable mammal. The test compound is evaluated for anti-cancer efficacy or tumor resistance-inducing activity, i.e., apoptosis activity as described herein. The uniqueness of testing potential therapeutic agents in this manner provides the following advantages: 1) because the diffusion chamber confines the cells, they can be examined for changes, either morphological or biochemical or molecular; 2) testing in this manner is quick, i.e., 24 to 48 hours, thus it can be also done with non-syngeneic tumor cells, since the testing is over before any immune reaction may occur; and 3) cells are much more sensitive to apoptotic agents in vivo than in vitro; contacting tumor cells in vitro often leads to the engagement of the apoptosis inducible machinery without a fully working apoptotic mechanism, thus resulting in lack of apoptosis; thus, these agents should be tested in vivo. Conditions that in vitro, in monolayer cultures, only result in inhibition of IGF-I-mediated growth, an inhibition often very modest, will cause massive (about 100-fold) apoptosis in vivo. Resnicoff, et al., *Cancer Res.*, 1995, 55, 2463; and Resnicoff, et al., *Cancer Res.*, 1995, 55, 3739.

Apoptosis can be determined by methods such as, for example, DNA ladder, electron or light microscopy, flow cytometry, and different commercially available kits for the determination of apoptosis. Thus, use of diffusion chambers to test agents for anti-cancer efficacy would save time and money and provide more accurate results that testing of the same agents in vitro. Tumor resistance-inducing activity can be examined by subsequent challenge of the mammal with tumor cells and evaluating the resistance of the mammal to the tumor cells as determined by inhibition of growth of the tumor cells.

The following examples are illustrative but are not meant to be limiting of the invention.

EXAMPLES

Example 1

General Procedures

Tumor Cell Lines

The C6 rat glioblastoma cell line was used in this experiment. The C6 cell line is syngeneic in BD-IX rats (Charles River Breeders Laboratories, Boston, Mass.). This cell line has been described in detail by Trojan, et al., *Science*, 1993, 259, 94–97; Resnicoff, et al., *Cancer Res.*, 35 1994a, 54, 2218–2222; Resnicoff, et al., *Cancer Res.*, 1994b, 54, 4848–4850; Trojan, et al., 1992, supra, the disclosures of which are hereby incorporated by reference in their entirety. Two cell lines derived from C6 cells were also used, one expressing an antisense RNA to the IGF-IR RNA, and a control one expressing a sense RNA. Both cell lines were characterized by Resnicoff, et al. (1994a, 1994b, supra), incorporated herein by reference in their entirety. Other cell lines used were a human melanoma cell line, FO-1, and a rat rhabdomyosarcoma cell line, BA 1112 (Martin, et al., *Eur. J. Cancer Clin. Oncol.*, 1983, 19, 791–797, incorporated herein by reference in its entirety). For FO-1 and BA 1112 cell lines, wild type cells were used, cells expressing sense and cells expressing antisense RNA to the IGF-IR RNA. The plasmids used and their effect on the number of IGF-I receptors have been described by Resnicoff, et al., *Cancer Res.*, 1994a, 5, 2218–2222, incorporated herein by reference in its entirety. The cells were pre-incubated at 39° C. for 24 hours, before inoculation in the diffusion chambers.

Cells were passaged in RPMI 1640 supplemented with, 5% calf serum and 5% fetal bovine serum. $8 \times 10^4$ cells were plated in 35 mm dishes in 10% serum; after 12 hours, the growth medium was removed and replaced with serum-free medium supplemented with 0.1% bovine serum albumin (fraction V) and 1.0 μM ferrous sulfate, with or without IGF-1 (10 ng/ml), as disclosed by Resnicoff, et al., *Cancer Res.*, 1994a, 5, 2218–2222, incorporated herein by reference in its entirety.

Balb/c 3T3 are 3T3 cells, passaged for several years, and p6 cells are Balb/c 3T3 cells stably transfected with, and overexpressing a human IGF-IR cDNA. Pietrzkowski, et al., *Cell Growth Diff.*, 1992a, 3, 199–205, incorporated herein by reference in its entirety. (tsA)R– and (tsA)R+ cells have been described by Sell, et al., *Proc. Natl. Acad. Sci. USA*, 1993, 90, 11217–11221. (tsa)R– cells have no IGF-I receptors, while (tsa)R+ 1 cells overexpress human IGF-IR cDNA. Both (tsa)R– and (tsa)R+ cells express SV40 T antigen.

The number of IGF-I receptors in cells expressing an antisense RNA to the IGF-IR RNA, or in wild type cells treated with antisense oligodeoxynucleotides, is decreased by about 60–70%. Pietrzkowski, et al., *Cell Growth Diff.*, 1992, 3, 199–205 and Resnicoff, et al., 1994a, 1994b, incorporated herein by reference in their entirety.

Oligodeoxynucleotides

The antisense oligodeoxynucleotide used is set forth in SEQ ID NO: 2, a DNA oligonucleotide to nucleotides –29 to –24 of the IGF-1R signal sequence. The control oligodeoxynucleotide was a mixture of random mismatchings at each nucleic acid position of the –29 to –24 signal sequence. Both oligonucleotides were phosphorothioates and were provided by Lynx Therapeutics (Hayward, Calif.).

The wild type C6 rat glioblastoma cells were incubated with antisense oligodeoxynucleotides to the IGF-IR RNA are shown in Table 1. The antisense oligonucleotide exerts a 50% inhibition in the growth of C6 cells, while the control oligonucleotide is totally inactive.

TABLE 1

Effect of an Antisense Oligodeoxynucleotide on the Growth of C6 Glioblastoma Cells in vitro

| conditions | number of cells $\times 10^4$ |
|---|---|
| serum-free medium | 21.0 ± 0.6 |
| serum-free medium + sense | 21.8 ± 0.5 |
| serum-free medium + antisense | 15.4 ± 0.9 |
| serum-free medium + IGF-I | 29.9 ± 0.7 |
| same + sense oligo | 28.4 ± 0.3 |
| same + antisense oligo | 13.4 ± 0.6 |

The number of cells was determined 48 hours after plating, and each number is the average (with standard deviation) of triplicates. The concentration of IGF-I was 10 ng/ml. The concentration of oligodeoxynucleotides was 120 μg/ml.

Diffusion Chamber

Diffusion chambers were constructed from 14 mm Lucite rings with 0.1 μm pore-sized hydrophilic Durapore membranes (Millipore, Bedford, Mass.). The diffusion chambers were sterilized with ethylene oxide prior to use. After the cells were pre-incubated for 24 hours according to the methods of Resnicoff, et al., 1994a, incorporated herein by reference in its entirety, and as set forth above, they were placed into the chambers, which were then inserted into the subcutaneous tissue of rats, under anesthesia with Halothane (inhalant). This procedure was repeated for C6 derivative cells expressing antisense RNA to IGF-IR RNA, C6 derivative cells expressing sense RNA to IGF-IR RNA, FO-1, and BA 11112 cell lines.

Aliquots of $5 \times 10^5$ cells were placed in diffusion chambers, that were then inserted in the subcutaneous tissue of syngeneic rats, and removed at various intervals thereafter. The number of cells in each chamber were counted, also the percentage of cells stained by trypan blue, and finally, the residual cells were plated in tissue culture dishes. Cells stably expressing the antisense RNA rapidly died in the diffusion chambers, most of the cells being dead after only 3 hours (FIG. 1), while wild type and sense cells doubled in number in 24 hours, at which time only an occasional antisense cell could still be recovered from the chambers.

Figure 2:
FIG. 2 shows a DNA ladder of apoptotic cells. Antisense C6 cells were placed in diffusion chambers for 40 minutes, the DNA was extracted and displayed as described in Example 1.

In one experiment, antisense C6 cells were suspended in 10% serum before placing them into a diffusion chamber; all the cells were dead by 24 hours. The antisense cells were examined for evidence of apoptosis by DNA extraction and visualization on ethidium bromide-stained gels. FIG. 2 shows the typical DNA ladder of apoptotic cells, from a sample taken 40 minutes after introduction of the antisense cells into the diffusion chambers.

When the wild type C6 cells, previously incubated with the antisense oligo, were placed in a diffusion chamber and inserted into the subcutaneous tissue of rats, the results were much more impressive, as most of the cells were dead by 24 hours (Table 2), whereas cells incubated with the control oligo doubled in number. These last two experiments indicate that the IGF-IR is even more important in vivo than in vitro, for protection from cell death.

Because cell death occurs so rapidly and because cells in a diffusion chamber are, at least in part, protected from an immune response, Lanza, et al., 1994, supra, incorporated herein by reference in its entirety, which at any rate, would not have the time to set in, other tumor cell lines were tested in the same breed of rats. The first one tested was the FO-1 human melanoma, and its two derivative cell lines, expressing either a sense or an antisense RNA to the IGF-IR. The results are summarized in Table 2; wild type human melanoma cells and sense cells doubled in 24 hours, whereas only 1% of the antisense expressing cells could be recovered after 24 hours. Other cell lines were tested, and the results are summarized also in Table 2. Note that the cell recovery is the real measure of growth and survival, since viability of the recovered cells (as determined by trypan blue) was close to 100%. These experiments show that: 1) cell death in diffusion chambers can also be achieved by pre-incubating the cells with antisense oligodeoxynucleotides to the IGF-IR RNA; and 2) that cell death in diffusion chambers can also be studied with non-syngeneic cell lines, in fact even with cells of other species. Thus, both wild type human melanoma cells, wild type rat rhabdomyosarcoma cells and murine p6 cells double in number after 24 hours in the diffusion chambers, while antisense melanoma and rhabdomyosarcoma cells and 3T3-like cells without IGF-IRs, die.

TABLE 2

Growth of Several Cell Lines in Diffusion Chambers

| cell line | percentage recovery |
|---|---|
| C6 rat glioblastoma | 195 |
| +random oligo | 189 |
| +antisense oligo | 0 |
| +etoposide | 0.025 |
| FO-1 human melanoma | |
| wild type | 200 |

TABLE 2-continued

Growth of Several Cell Lines in Diffusion Chambers

| cell line | percentage recovery |
|---|---|
| sense plasmid | 200 |
| antisense plasmid | 1.4 |
| BA 1112 rat rhabdomyosarcoma | |
| wild type | 200 |
| sense plasmid | 200 |
| antisense plasmid | 0 |
| B1792-F10 mouse melanoma | |
| wild type | 214 |
| sense plasmid | 198 |
| antisense plasmid | 0 |
| mouse melanoma B16 | |
| wild type | 214 |
| sense plasmid | 198 |
| antisense plasmid | 0.10 |
| p6 cells (3T3 overexpressing the IGF-IR) | 186 |
| T/R− (receptorless 3T3) | 0 |

The C6 rat glioblastoma cells were wild type cells treated or not with oligodeoxynucleotides (120 mg/ml, 24 hours before inoculation). In the case of etoposide (20 μg/ml), the C6 cells were pre-incubated with the drug for 16 hrs, prior to loading into the diffusion chamber, at which time viability was 100%. Human melanoma cells were wild type or stably transfected with either a sense or an antisense expression plasmid to the IGF-IR RNA. BA 1112 also consisted of the original wild type cell line, or cell lines stably transfected with either sense or antisense plasmids to the IGF-IR RNA. p6 cells are derived from Balb/c 3T3 cells, and express over $5 \times 10^5$ IGF-IRs per cell (Pietrzkowski, et al., 1992a, 1992b), incorporated herein by reference in their entirety; T/R− cells are 3T3 cells, derived from mouse embryos with a targeted disruption of the IGF-IR genes. Sell, et al., *Proc. Natl. Acad. Sci. USA*, 1993, 90, 11217–11221 and Sell, et al., *Mol. Cell. Biol.*, 1994, 14, 3604–3612, incorporated herein by reference in their entirety. The percentage changes are after 24 hours in diffusion chambers in rats.

Growth Curves $5 \times 10^4$ C6 cells were plated in 35 mm dishes in 10% serum; after 4 hours the growth medium was removed and replaced with serum-free medium, supplemented with 0.1% bovine serum albumin (fraction V) and 1 μM ferrous sulfate, with or without IGF-I (10 μg/ml). Random or antisense oligodeoxynucleotides (Lynx Therapeutics, Hayward, Calif.) were added at a concentration of 120 μg/ml, directly to the medium. The cells were counted after 24 and 48 hours, using a hemocytometer. Viability was determined by trypan blue exclusion. This procedure was repeated for C6 derivative cells expressing antisense RNA to IGF-IR RNA and C6 derivative cells expressing sense RNA to IGF-IR RNA, FO-1, and BA 11112 cell lines.

Plating of cells resulted in rapid overgrowth with the wild type and sense cells, whereas antisense cells, after 24 hours in the diffusion chambers, did not produce any colony in vitro.

Determination of Apoptosis

Cells were lysed in 50 μl of lysis buffer (10 mM EDTA, 50 mM Tris pH 8,0.5% sodium dodecyl sulfate, 0.5 mg/ml proteinase K). RNAse A (0.5 mg/ml) was added and lysates were incubated for 1 hr. at 37. Two phenol extraction (equal volumes) were performed, followed by one chloroform extraction. DNA was precipitated with two volumes of ice-cold ethanol and incubated at −80° C. for 1 hr. DNA was pelleted by centrifugation at 14,000 rpm for 10 minutes at 4° C. Pellets were air-dried for 30 minutes, resuspended in 50 μl of Tris-EDTA pH 8. DNA was electrophoresed in a 1.8% agarose gel in 1×TBE running buffer (0.05 M Tris base, 0.05 M boric acid, 1 mM disodium EDTA), according to the methods of Preston, et al., *Cancer Res.*, 1994, 54, 4214–4223, incorporated herein by reference in its entirety.

Example 2

Protective And Curative Effects Against Tumor Growth By Apoptotic Cells In Diffusion Chambers C6 cells constitutively expressing an antisense RNA to the IGF-IR RNA and C6 cells pre-treated for 24 hours with antisense oligodeoxynucleotides of SEQ ID NO: 2 (−29 to −24 of the signal sequence) to the same RNA (at a concentration of 120 μg/ml) were inoculated into diffusion chambers ($5 \times 10^5$ cells per chamber in 0.2 ml of phosphate buffered saline), which were then inserted into the subcutaneous tissue of 7-week-old male BD-IX rats (Charles River Breeders Laboratories, Boston, Mass.). Untreated C6 cells, C6 cells expressing a sense RNA, and C6 cells pre-treated with a randomly mismatched oligodeoxynucleotide at each nucleic acid position of the −29 to 24 signal sequence were used as controls. Since these 3 groups of cells behaved in exactly the same manner, they are included into a single control group.

The diffusion chambers were removed at various intervals after insertion, ranging from 15 minutes to 48 hours. Seven days later, the rats were challenged with $10^7$ wild type C6 cells, injected above the right hind leg.

The results are summarized in Table 3. The first column (cells in diffusion chamber) indicates the treatment; the second column (% recovery) reveals the number of cells recovered expressed as percentage of cells inoculated; and the 3rd column (tumor development) gives the number of rats with tumors after challenging the animals, previously carrying the diffusion chambers, with $10^7$ wild type C6 cells, subcutaneously.

TABLE 3

| cells in diffusion chambers | % recovery | tumor development |
|---|---|---|
| control group | 200 | 15/15 (day 5) |
| antisense transfected 45 minutes | 65 | 9/9 (day 5) |
| antisense transfected 3 hours | 0–4 | 0/12 |
| antisense oligos 24 hours | 0 | 0/3 |

The first column indicates the times (in minutes and hours), after insertion, when the diffusion chambers were removed. The second column gives the percentage of live cells that were recovered. The third column reveals the appearance of wild type tumors after the rats that had received the diffusion chamber were challenged with C6 cells. Day 5 in the 3rd column is the latent period, after injection of wild type cells, for the appearance of a palpable tumor.

This example shows that resistance against subsequent challenge with homologous wild type tumor cells can be achieved either by placing in diffusion chambers cells transfected with a plasmid expressing an antisense RNA. to the IGF-IR RNA (Resnicoff, et al., 1994a, 1994b, supra.), incorporated by reference in its entirety, or by pre-treatment of wild type cells with antisense oligonucleotides to the IGF-IR RNA. They also indicate that resistance is conferred, when some cells are still alive (diffusion chamber left in the rat for 3 hours), i.e. it is not necessary for all cells in the chamber to die to induce resistance.

Example 3

Regression Of Established Tumors By Apoptotic Cells In Diffusion Chambers

The expression plasmids used, and the C6 cells and their derivatives used in these experiments have been described in detail in papers by Resnicoff, et al., 1994a, 1994b, supra.), incorporated by reference in their entirety. The oligodeoxynucleotide sequences are provided by Resnicoff, et al., the antisense was originally described in Pietrzkowski, et al. 1992a, 1992b, supra, incorporated by reference in their entirety.

$10^7$ wild type C6 cells were injected subcutaneously above the right hind leg of 7-week-old male BD-IX rats. Tumors appeared at day 5, as usual. On day 7, some animals, selected at random, received diffusion chambers containing $5 \times 10^5$ C6 cells constitutively expressing an antisense RNA to the IGF-IR RNA (Resnicoff, et al., 1994a, 1994b). After 24 hours, the diffusion chambers were removed, and no cells could be recovered from them. Five days later, the rats who received the diffusion chambers had tumors considerably smaller than the control animals (no chambers). Seven days after removal of the diffusion chambers (14 days after injection of wild type cells), the results were as follows:

TABLE 4

| condition | tumor development |
|---|---|
| control rats | 3/3 |
| treated rats | 0/3 |

Control rats were injected with $10^7$ wild type C6 cells and did not receive a diffusion chamber; treated rats received, 7 days after injection of wild type cells, a diffusion chamber with $5 \times 10^5$ C6 cells expressing an antisense RNA of SEQ ID NO: 1, to nucleic acids positions 1 to 309 to the IGF-IR RNA of FIGS. 4A–4G. In treated rats, no residual tumor could be detected at autopsy (histological examination).

This example shows that homologous tumor cells, expressing an antisense RNA to the IGF-IR RNA, inoculated into diffusion chambers, induces regression of already well established wild type tumors.

Example 4

Induction Of resistance To Tumor Cells

The extent to which the tumor cells undergoing apoptosis in the diffusion chambers protect rats from the subsequent challenge with wild type C6 cells is shown in this experiment. For this purpose, different, non-syngeneic and non-homologous types of cells were inserted as usual in diffusion chambers, for a period of 24 hours. The chambers were removed, monitored for recovery of cells, and the rats were subsequently challenged with $10^7$ wild type C6 cells, following the same protocols described above. The results are summarized in Table 5, where subsequent to challenge, (−)=no tumor, (+)=no regression.

TABLE 5

| cell type in chambers | % recovery | tumor development |
|---|---|---|
| Human melanoma cells (antisense) | 1.4 | (−) |
| BA-1112 (antisense) | 0 | (−) |
| (tsA)R− | 0 | (−) |
| Balb/c3T3 | 0.8 | (+) |
| (tsA)R+ | 3.2 | (+) |
| C6 cells + etoposide | 0.025 | (−) |

Human melanoma cells are FO-1 cells expressing an antisense RNA to the IGF-IR RNA (Resnicoff, et al. 1994a, 1994b, incorporated by reference in their entirety); BA-1112 are cells from a transplantable rat sarcoma, also expressing an antisense RNA to the IGF-IR RNA; (tsA)R−, Balb/c 3T3 and (tsA)R+ are 3T3-like mouse cells, described in detail in Sell, et al., 1994, supra., incorporated herein by reference in its entirety; C6 cells + etoposide, are wild type C6 cells pre-treated for 16 hrs with the topoisomerase inhibitor, etoposide. At the moment of loading the chamber, cells pre-treated with etoposide (20 μg/ml) were 100% viable. After 24 hrs, in vivo, only 125 cells could be recovered, of which 50% were viable, from which the percent recovery was calculated.

These experiments show that, curiously enough, when the cells placed in the diffusion chambers lacked the IGF-IR or had markedly reduced numbers, they protected rats from a subsequent challenge with wild type C6 rat glioblastoma cells, regardless of the species of cells used in the chambers. Cells with a normal number of IGF-I receptors, under the same conditions, did not display a protective effect. This seems to indicate that the protective effect of antisense strategies against the IGF-I receptor RNA cuts across species barriers.

Example 5

Induction Of Tumor Resistance With Pro-Apoptotic Agents

In the following experiments, cells were cultured in vitro in the presence of the particular pro-apoptotic agent for 24 hours. The tumor cells were detached from the culture plates, washed three times with phosphate buffered saline (PBS) and resuspended in PBS prior to being placed in diffusion chambers, as described in Resnicoff, et al., *Cancer Res.*, 1995, 55, 2463–2469, incorporated herein by reference. The diffusion chambers were subsequently implanted into the subcutaneous tissue in rats or mice. Twenty four hours later, the cells were recovered from the diffusion chambers, stained with trypan blue, and counted in a hemocytometer. The results are shown in Table 6, and are given as percentage of cells undergoing apoptosis and induction of tumor resistance.

TABLE 6

| Condition | Apoptosis (%) | Induction of Tumor Resistance |
|---|---|---|
| C6 rat glioblastoma + soluble IGF-IR | 95 | YES |
| CaOV-3 human ovarian carcinoma + MyCF | 99 | YES |
| MHC Class I peptides ($10^{-5}$ to $10^{-8}$M) + ovarian carcinoma | 90 to 96.5 | YES |
| glioblastoma | 95 | YES |
| colon carcinoma | 30 | not tested |
| small cell lung carcinoma | 30 | not tested |
| melanoma | 25 | not tested |
| C6 rat glioblastoma + etoposide (20 μM/16 hours) | 99.975 | YES |
| camptothecin (5 × $10^{-9}$ M/6 hours) | 95 | YES |
| mouse sarcoma + etoposide (20 μM/16 hours) | 98 | not tested |
| P6 mouse fibroblasts + TNF-60 (10 pg/6 hours) | 99.9 | not tested |

Example 6

Testing Agents For Anti-Cancer Activity In Vivo Using Diffusion Chambers

As set forth above, the present invention provides an in vivo method of screening agents for anti-cancer therapeutic activity, such as, for example, apoptosis activity. Tumor cells in media in vitro are supplemented with a test compound for a period of time between 3 hours and 48 hours, preferably 24 hours. After in vitro culture, the tumor cells are placed in a diffusion chamber, which is subsequently implanted into a test animal, such as a rat or mouse, or other suitable mammal. Alternatively, the tumor cells are cultured in the absence of a test compound. The tumor cells are transferred to a diffusion chamber which is implanted into a mammal, and the mammal is given the test compound. The test compound is evaluated for anti-cancer efficacy, i.e., apoptosis activity as described herein, and he effect of the test compound on induction of tumor resistance is also evaluated.

Tumor cells that may be used in the diffusion chamber include any cells capable of being inhibited by anti-cancer agents, i.e., undergoing apoptosis when exposed to an anti-cancer agent or pro-apoptotic agent. Such cells include, but are not limited to rat glioblastoma, human glioblastoma, human melanoma, human breast carcinoma, human lung carcinoma, mouse melanoma, mouse leukemia, human ovarian carcinoma, human rhabdomyosarcoma, rat rhabdomyosarcoma, pancreatic carcinoma cells, C6 rat glioblastoma, and the like, as well as those disclosed above. It is contemplated that any cancer cell may be used to test the anti-cancer efficacy of a test agent.

Tumor cells can be placed in a diffusion chamber in varying amounts. Preferably, about $1 \times 10^4$ to about $5 \times 10^6$ cells can be placed in the diffusion chamber. More preferably, about 105 to about $1.5 \times 10^6$ cells can be placed in the diffusion chamber. Most preferably, about $5 \times 10^5$ cells are placed in the chamber. The cells are placed in the diffusion chamber containing media. It is contemplated that any media that supports the growth of cancer cells can be used.

Test agents may be administered to individuals as a single or in multiple doses. Preferred for pharmaceutical compositions that comprise the test agents in combination with a pharmaceutically acceptable carrier or diluent. The pharmaceutical compositions may be administered by any means that enables the active agent to reach the diffusion chamber in the body of animal. Agents may be administered orally, or by parenteral administration, i.e., intravenous, subcutaneous, intramuscular depending on their chemical or physical nature. In some preferred embodiments, pharmaceutical compositions which comprise the agents are administered intravenously or subcutaneously. Pharmaceutical compositions may be administered either as individual therapeutic agents or in combination with other therapeutic agents. They can be administered alone, but are generally administered with a pharmaceutical carrier selected on the basis of the chosen route of administration and standard pharmaceutical practice. The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. A test agent is placed in the in vitro tumor cell culture prior to washing the cells and placing them inside a diffusion chamber or delivered to the test animal outside the chamber at a variety of concentrations ranging from about 1 picogram to about 1 g. In some embodiments, test agents may be used at a concentration of about 1 $\mu$g to about 100 $\mu$g. Usually a daily dosage of active ingredient can be about 1 pg to 1 grams per kilogram of body weight, in some embodiments about 0.1 pg to 100 mg per kilogram of body weight. Ordinarily dosages are in the range of 0.5 to 50 milligrams per kilogram of body weight, and preferably 1 to 10 milligrams per kilogram per day. In some embodiments, the pharmaceutical compositions are given in divided doses 1 to 6 times a day or in sustained release form is effective to obtain desired results. Dosage forms (composition) suitable for internal administration generally contain from about 1 milligram to about 500 milligrams of active ingredient per unit. In these pharmaceutical compositions the active ingredient will ordinarily be present in an amount of about 0.5–95 by weight based on the total weight of the composition.

For parenteral administration, the test compound can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

Suitable pharmaceutical carriers are described in the most recent edition of *Remington's Pharmaceutical Sciences*, A. Osol, a standard reference text in this field. For example, a parenteral composition suitable for administration by injection is prepared by dissolving 1.5% by weight of active ingredient in 0.9% sodium chloride solution.

Peptides and proteins may be delivered in protein form or provided by expression vectors or by infection through virions. One skilled in the art is readily able to deliver test agents by numerous methods widely known to those skilled in the art. Test agents may be delivered alone or in combination with other test agents.

The diffusion chamber containing tumor cells treated with or without the test agent(s) is implanted into a mammal, preferably a rat or mouse. The mammal can be tumor-free, or can be tumor-expressing. Tumor-expressing mammals include those which express tumors naturally, or those in which tumor cells are injected. The diffusion chamber is implanted subcutaneously or intraperitoneally, for example, in tumor-free or tumor-expressing mammals. The chamber may be removed about 6 to about 96 hours after implantation. Preferably, the chamber is removed about 12 to about 72 hours after implantation. More preferably, the chamber is removed about 18 to about 48 hours after implantation. Most preferably, the chamber is removed about 24 to about 30 hours after implantation. It is contemplated that a range of times will be used to establish optimum activity of the test compound. Alternatively, a refillable chamber may be employed such that the chamber may be re-used for treatments and emptied following treatments. Anti-cancer efficacy can be evaluated by determining the extent of growth inhibition or death of tumor cells in the diffusion chamber. In addition, mice or rats with naturally growing tumors or those injected with tumor cells can be implanted as described above. The effect of the test agent on tumor cells outside the diffusion chamber can be determined as described above. Apoptosis can be determined by methods such as, for example, DNA ladder, electron or light microscopy, flow cytometry, and different commercially available kits for the determination of apoptosis.

Example 7

Induction Of Resistance To Melanoma

C57/BL6 mice were injected subcutaneously with $10^5$ B1792-F10 mouse melanoma cells. The cells were either untreated or pretreated for 24 hours prior to injection with either sense or antisense oligonucleotides to IGF-IR. Mice were injected a second time into the left flank. The size of the tumors at the time of the second injection was 2 to 2.5 grams. The results of this experiment are shown in Table 7.

TABLE 7

| cells injected first injection (right flank) | second injection (left flank) | tumor development number of animals (palpable tumors in days) |
|---|---|---|
| untreated | | 6/6 (4–5) dead by day 16 |
| sense | | 6/6 (5–6) dead by day 18 |
| antisense | | 0/6 (negative at day 62) |
| sense | untreated | 3/3 bilateral tumors |
| antisense | untreated | 0/3 (negative at day 55) |
| untreated | sense | 3/3 dead by day 15–16 |
| untreated | antisense | 3/3 (same tumor weight for 1 month) |

Example 8

Induction Of Melanoma Tumor Resistance

C57/BL6 mice were first treated with cells placed in a diffusion chamber that was inserted into the subcutaneous tissue and removed after 24 hours. B1792-F10 mouse melanoma cells were either untreated or treated with random or antisense oligonucleotides to IGF-IR. One week after the removal of the diffusion chamber, the mice were challenged with $10^5$ untreated cells, and observed for the appearance of tumors. The results of this experiment are shown in Table 8.

TABLE 8

| condition | recovery (%) | protection against challenge with untreated cells |
|---|---|---|
| untreated | 218 | NO (tumors appeared on day 5) |
| random oligonucleotide 13 µM | 209 | NO (tumors appeared at day 5) |
| antisense oligonucleotide 13 µM | 114 | partial protection (tumors appeared at day 12) |
| random oligonucleotide 19 µM | 196 | NO (tumors appeared at day 5) |
| antisense oligonucleotide 19 µM | 0.1 | YES (no tumors for greater than 1 month) |

Example 9

Induction of Resistance With MHC Class I Peptides;

C6 cells were incubated with an MHC Class I associated peptide at several concentrations for 24 hours in medium before injection ($10^5$ cells in 0.1 ml) into the subcutaneous tissue of 7-week-old male Balb/c mice. Percentage recovery based on the initial inoculum was determined in parallel experiments using diffusion chambers. Diffusion chambers were removed from the animals after 24 hours and viable cell were quantified by trypan blue exclusion. The results are presented in Table 9.

TABLE 9

| Treatment | Recovery (%) | Expected delay (days) | Palpable Tumors (days) |
|---|---|---|---|
| None | 212.0 ± 2.0 | 4 | 4 |
| control peptide ($10^{-5}$M) | 208.0 ± 1.3 | 4 | 4 |
| peptide ($10^{-12}$M) | 18.0 ± 0.6 | 8 | 11 |
| peptide ($10^{-10}$M) | 4.5 ± 0.2 | 10 | 14 |
| peptide ($10^{-8}$M) | 2.1 ± 0.1 | 11 | 14 |
| peptide ($10^{-5}$M) | 0.3 ± 0.01 | 14 | 21 |

The control peptide had the amino acid sequence Tyr-Leu-Glu-Pro-Gly-Ala-Val-Thr-Ala (SEQ ID NO: 15). The peptide used in the experiments had the amino acid sequence Tyr-Leu-Arg-Pro-Gly-Pro-Val-Thr-Ala (SEQ ID NO: 16). Expected delay is the number of days after injection before the tumors should become palpable, based on survival in vivo estimated by percentage of cells recovered. The last column gives the actual number of days after injection when tumors become palpable. Three nude mice were used for each experimental condition.

In another experiment, CaOV-3 human ovarian carcinoma cells ($5 \times 10^5$ cells) were implanted in diffusion chambers in the subcutaneous tissue of mice. MHC Class I associated peptides were injected subcutaneously (0.2 ml of a $5 \times 10^5$ M solution) simultaneous and adjacent to the diffusion chambers. Three mice were used for each experimental condition. The results are shown in Table 10 below.

TABLE 10

| peptide | recovery (% at 24 hours) |
|---|---|
| peptide (SEQ ID NO: 16) | 3.0 ± 0.1 |
| peptide (SEQ ID NO: 10) | 0.2 ± 0.01 |
| peptide (SEQ ID NO: 14) | 6.6 ± 0.2 |
| control peptide (SEQ ID NO: 15) | 280.0 ± 8.4 |

Various modifications of the invention in addition to those shown and described herein will be apparent to those skilled in the art from the foregoing description. Such modifications are also intended to fall within the scope of the appended claims.

What is claimed is:

1. A method of inducing resistance to tumor growth in a mammal comprising:
    a) pretreating tumor cells in vitro with an MHC class I-associated peptide comprising a Pro-Gly-Pro motif;
    b) placing said pretreated tumor cells in a diffusion chamber, thereby producing a tumor cell-containing diffusion chamber; and
    c) inserting said tumor cell-containing diffusion chamber into said mammal for a therapeutically effective time, thereby inducing resistance to tumor growth.

2. The method of claim 1 wherein said peptide comprises an amino acid sequence selected from the group consisting of SEQ ID NO:10, SEQ ID NO:13, and SEQ ID NO:16.

3. The method of claim 2 wherein said peptide comprises SEQ ID NO:16.

4. The method of claim 1 wherein a therapeutically effective time is a time permitting death of said tumor cells in said cell-containing chamber and resistance of said tumor growth in said mammal.

5. The method of claim 1 wherein said tumor cells are excised from said mammal prior to pre-treatment.

6. The method of claim 1 wherein said pretreated tumor cells are selected from the group consisting of autografts of tumor cells, allografts of tumor cells, syngeneic tumor cells, non-syngeneic tumor cells, and xenografts of tumor cells.

7. The method of claim 1 wherein said pretreated tumor cells are selected from the group consisting of glioblastoma tumor cells, pancreatic tumor cells, melanoma tumor cells, prostate tumor cells, ovary tumor cells, mammary tumor cells, lungs tumor cells, colon tumor cells, and smooth muscle tumor cells.

8. The method of claim 1 wherein said mammal is human.

9. A method of inducing resistance to tumor growth in a mammal comprising:
    a) pretreating tumor cells in vitro with etoposide or camptothecin;
    b) placing said pretreated tumor cells in a diffusion chamber, thereby producing a tumor cell-containing diffusion chamber; and
    c) inserting said tumor cell-containing diffusion chamber into said mammal for a therapeutically effective time, thereby inducing resistance to tumor growth.

10. A method of screening pro-apoptotic agents for anti-cancer activity in a mammal having cancer comprising the steps of:
    a) providing an in vitro tumor cell culture supplemented with said pro-apoptotic agent;
    b) placing said tumor cells from step a) into a diffusion chamber, thereby producing a tumor cell-containing diffusion chamber;
    c) inserting said tumor cell-containing difusion chamber into said mammal for a period of time; and
    d) removing said tumor cell-containing diffusion chamber and evaluating the anti-cancer effects of said pro-apoptotic agent by determining the tumor resistance-inducing activity in said mammal.

11. The method of claim 10 wherein said determining the tumor resistance-inducing activity in said mammal comprises determining the inhibition of growth of the tumor cells or the presence or absence of tumors in said mammal.

12. A method of screening pro-apoptotic agents for anti-cancer activity in a mammal having cancer comprising the steps of:
    a) providing an in vitro tumor cell culture supplemented with said pro-apoptotic agent;
    b) placing said tumor cells from step a) into a diffusion chamber, thereby producing a tumor cell-containing diffusion chamber;
    c) inserting said tumor cell-containing diffusion chamber into said mammal for a period of time; and
    d) removing said tumor cell-containing diffusion chamber and evaluating the anti-cancer effects of said pro-apoptotic agent by evaluating apoptosis of said tumor cells in said diffusion chamber and the presence or absence of tumors in said mammal.

13. A method of inducing resistance to tumor growth in a mammal comprising:
    a) pretreating tumor cells in vitro with a pro-apoptotic agent selected from the group consisting of an anti-sence oligonucleotide comprising SEQ ID NO:2, myristylated C-terminus insulin growth factor-1 receptor, and soluble insulin growth factor-1 receptor;
    b) placing said pretreated tumor cells in a diffusion chamber, thereby producing a tumor cell-containing diffusion chamber; and
    c) inserting said tumor cell-containing diffusion chamber into said mammal for a therapeutically effective time, thereby inducing resistance to tumor growth.

14. The method of claim 13 wherein said tumor cells are pretreated with a vector which produces said oligonucleotide.

15. The method of claim 13 wherein a therapeutically effective time is a time permitting death of said tumor cells in said cell-containing chamber and resistance of said tumor growth in said mammal.

16. The method of claim 13 wherein said tumor cells are excised from said mammal prior to pre-treatment.

17. The method of claim 13 wherein said pretreated tumor cells are selected from the group consisting of autografts of tumor cells, allografts of tumor cells, syngeneic tumor cells, non-syngeneic tumor cells, and xenogrofts of tumor cells.

18. The method of claim 13 wherein said pretreated tumor cells are selected from the group consisting of glioblastoma tumor cells, pancreatic tumor cells, melanoma tumor cells, prostate tumor cells, ovary tumor cells, mammary tumor cells, lungs tumor cells, colon tumor cells, and smooth muscle tumor cells.

19. The method of claim 13 wherein said mammal is human.

* * * * *

SEQUENCE LISTING

<160> NUMBER OF SEQ ID NOS: 18

<210> SEQ ID NO 1
<211> LENGTH: 927
<212> TYPE: RNA
<213> ORGANISM: Artificial Sequence
<220> FEATURE:
<221> NAME/KEY: misc_feature
<223> OTHER INFORMATION: Novel Sequence

<400> SEQUENCE: 1

| | | | | | | |
|---|---|---|---|---|---|---|
| cuuuguuuuc | uuuucuuccu | cacagaccuu | cgggcaagga | ccuucacaag | ggaugcagua | 60 |
| caugcucugg | cugccguugc | ggaugaagcc | cgaggggcac | uccugcaugc | acucgccguc | 120 |
| guggaucaca | aaccccucgg | agucgcugcu | cucggcgcug | aggauguugg | cgcagaaguc | 180 |
| acguccaca | cagcgccagc | ccucaaaccu | guagguguug | ggcgggcagg | caggcacaca | 240 |
| gacaccggca | uaguaguagu | ggcggcaagc | uacacaggcc | gugucguugu | caggcgcgcu | 300 |
| gcagcugccc | aggcacucgg | gguggcagca | cucauuguuc | ucggugcacg | cccgcuuccc | 360 |

-continued

```
acacgugcuu gggcacauuu ucuggcagcg guuugugguc cagcagcggu aguuguacuc      420
auuguugaug gugucuucu cacacaucgg cuucccucc augucccug gacacagguc         480 cccacauucc uuuggggcu auucccac aauguaguua uggacaccg cauccaggau          540 cagggaccag uccacagugg agagguaaca gaggucagca uuuuucacaa uccugauggc      600
cccccgagua auguuccuca gguuguaaag cccaauauc uugagauugg ucaucucgaa       660
gaugaccagg gcguaguugu agaagaguuu ccagccgcgg augaccguga gguuggggaa      720 gagucuccg aggcucucga ggccagccac ucgaacagc agcaaguacu cgguaaugac        780
cgugagcuug gggaagcggu agcugcggua guccucggcc uuggagauga gcaggaugug     840
gagguagccc ucgaucaccg ugcaguucuc caggcgcuuc agcugcugau agucguugcg     900
gaugucgaug ccuggcccgc agauuuc                                         927
```

<210> SEQ ID NO 2
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence
<400> SEQUENCE: 2

```
tcctccggag ccagactt                                                    18
```

<210> SEQ ID NO 3
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence
<400> SEQUENCE: 3

```
ggaccctcct ccggagcc                                                    18
```

<210> SEQ ID NO 4
<211> LENGTH: 17
<212> TYPE: DNA
<213> ORGANISM: Artificial Sequence
<220> FEATURE:
<221> NAME/KEY: misc_feature
<223> OTHER INFORMATION: Novel Sequence
<400> SEQUENCE: 4

```
ccggagccag acttcat                                                     17
```

<210> SEQ ID NO 5
<211> LENGTH: 20
<212> TYPE: DNA
<213> ORGANISM: Artificial Sequence
<220> FEATURE:
<221> NAME/KEY: misc_feature
<223> OTHER INFORMATION: Novel Sequence
<400> SEQUENCE: 5

```
ctgctcctcc tctaggatga                                                  20
```

<210> SEQ ID NO 6
<211> LENGTH: 15
<212> TYPE: DNA
<213> ORGANISM: Artificial Sequence
<220> FEATURE:

```
<221> NAME/KEY: misc_feature
<223> OTHER INFORMATION: Novel Sequence

<400> SEQUENCE: 6
ccctcctccg gagcc                                                   15

<210> SEQ ID NO 7
<211> LENGTH: 17
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 7
tacttcagac cgaggcc                                                 17

<210> SEQ ID NO 8
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 8
ccgaggcctc ctcccagg                                                18

<210> SEQ ID NO 9
<211> LENGTH: 18
<212> TYPE: DNA
<213> ORGANISM: Artificial Sequence
<220> FEATURE:
<221> NAME/KEY: misc_feature
<223> OTHER INFORMATION: Novel Sequence

<400> SEQUENCE: 9
tcctccggag ccagactt                                                18

<210> SEQ ID NO 10
<211> LENGTH: 9
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 10

Tyr Leu Glu Pro Gly Pro Val Thr Ala
1               5

<210> SEQ ID NO 11
<211> LENGTH: 10
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 11

Leu Leu Asp Gly Thr Ala Thr Leu Arg Leu
1               5                   10

<210> SEQ ID NO 12
<211> LENGTH: 9
<212> TYPE: PRT
<213> ORGANISM: Artificial Sequence
```

```
<220> FEATURE:
<221> NAME/KEY: misc_feature
<223> OTHER INFORMATION: Novel Sequence

<400> SEQUENCE: 12

Phe Glu Cys Asn Thr Ala Gln Pro Gly
1               5

<210> SEQ ID NO 13
<211> LENGTH: 9
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 13

Ala Thr Val Pro Gly Pro Glu Leu Tyr
1               5

<210> SEQ ID NO 14
<211> LENGTH: 10
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 14

Leu Arg Leu Thr Ala Thr Gly Asp Leu Leu
1               5                   10

<210> SEQ ID NO 15
<211> LENGTH: 9
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 15

Tyr Leu Glu Pro Gly Ala Val Thr Ala
1               5

<210> SEQ ID NO 16
<211> LENGTH: 9
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 16

Tyr Leu Arg Pro Gly Pro Val Thr Ala
1               5

<210> SEQ ID NO 17
<211> LENGTH: 4989
<212> TYPE: DNA
<213> ORGANISM: Artificial Sequence
<220> FEATURE:
<221> NAME/KEY: misc_feature
<223> OTHER INFORMATION: Novel Sequence
<221> NAME/KEY: CDS
<222> LOCATION: (46)..(4146)

<400> SEQUENCE: 17 ttttttttttt ttttgagaaa gggaatttca tcccaaataa aagga atg aag tct ggc      57
```

```
                        Met Lys Ser Gly
                         1 tcc gga gga ggg tcc ccg acc tcg ctg tgg ggg ctc ctg ttt ctc tcc    105
Ser Gly Gly Gly Ser Pro Thr Ser Leu Trp Gly Leu Leu Phe Leu Ser
 5           10              15                  20 gcc gcg ctc tcg ctc tgg ccg acg agt gga gaa atc tgc ggg cca ggc    153
Ala Ala Leu Ser Leu Trp Pro Thr Ser Gly Glu Ile Cys Gly Pro Gly
             25              30                  35 atc gac atc cgc aac gac tat cag cag ctg aag cgc ctg gag aac tgc    201
Ile Asp Ile Arg Asn Asp Tyr Gln Gln Leu Lys Arg Leu Glu Asn Cys
         40              45                  50 acg gtg atc gag ggc tac ctc cac atc ctg ctc atc tcc aag gcc gag    249
Thr Val Ile Glu Gly Tyr Leu His Ile Leu Leu Ile Ser Lys Ala Glu
                 55              60                  65 gac tac cgc agc tac cgc ttc ccc aag ctc acg gtc att acc gag tac    297
Asp Tyr Arg Ser Tyr Arg Phe Pro Lys Leu Thr Val Ile Thr Glu Tyr
 70              75                  80 ttg ctg ctg ttc cga gtg gct ggc ctc gag agc ctc gga gac ctc ttc    345
Leu Leu Leu Phe Arg Val Ala Gly Leu Glu Ser Leu Gly Asp Leu Phe
85              90                  95                  100 ccc aac ctc acg gtc atc cgc ggc tgg aaa ctc ttc tac aac tac gcc    393
Pro Asn Leu Thr Val Ile Arg Gly Trp Lys Leu Phe Tyr Asn Tyr Ala
                 105                 110                 115 ctg gtc atc ttc gag atg acc aat ctc aag gat att ggg ctt tac aac    441
Leu Val Ile Phe Glu Met Thr Asn Leu Lys Asp Ile Gly Leu Tyr Asn
             120                 125                 130 ctg agg aac att act cgg ggg gcc atc agg att gag aaa aat gct gac    489
Leu Arg Asn Ile Thr Arg Gly Ala Ile Arg Ile Glu Lys Asn Ala Asp
             135                 140                 145 ctc tgt tac ctc tcc act gtg gac tgg tcc ctg atc ctg gat gcg gtg    537
Leu Cys Tyr Leu Ser Thr Val Asp Trp Ser Leu Ile Leu Asp Ala Val
         150                 155                 160 tcc aat aac tac att gtg ggg aat aag ccc cca aag gaa tgt ggg gac    585
Ser Asn Asn Tyr Ile Val Gly Asn Lys Pro Pro Lys Glu Cys Gly Asp
165                 170                 175                 180 ctg tgt cca ggg acc atg gag gag aag ccg atg tgt gag aag acc acc    633
Leu Cys Pro Gly Thr Met Glu Glu Lys Pro Met Cys Glu Lys Thr Thr
             185                 190                 195 atc aac aat gag tac aac tac cgc tgc tgg acc aca aac cgc tgc cag    681
Ile Asn Asn Glu Tyr Asn Tyr Arg Cys Trp Thr Thr Asn Arg Cys Gln
         200                 205                 210 aaa atg tgc cca agc acg tgt ggg aag cgg gcg tgc acc gag aac aat    729
Lys Met Cys Pro Ser Thr Cys Gly Lys Arg Ala Cys Thr Glu Asn Asn
     215                 220                 225 gag tgc tgc cac ccc gag tgc ctg ggc agc tgc agc gcg cct gac aac    777
Glu Cys Cys His Pro Glu Cys Leu Gly Ser Cys Ser Ala Pro Asp Asn
 230                 235                 240 gac acg gcc tgt gta gct tgc cgc cac tac tat gcc ggt gtc tgt        825
Asp Thr Ala Cys Val Ala Cys Arg His Tyr Tyr Tyr Ala Gly Val Cys
245                 250                 255                 260 gtg cct gcc tgc ccg ccc aac acc tac agg ttt gag ggc tgg cgc tgt    873
Val Pro Ala Cys Pro Pro Asn Thr Tyr Arg Phe Glu Gly Trp Arg Cys
             265                 270                 275 gtg gac cgt gac ttc tgc gcc aac atc ctc agc gcc gag agc agc gac    921
Val Asp Arg Asp Phe Cys Ala Asn Ile Leu Ser Ala Glu Ser Ser Asp
             280                 285                 290 tcc gag ggg ttt gtg atc cac gac ggc gag tgc atg cag gag tgc ccc    969
Ser Glu Gly Phe Val Ile His Asp Gly Glu Cys Met Gln Glu Cys Pro
             295                 300                 305
```

-continued

| | | |
|---|---|---|
| tcg ggc ttc atc cgc aac ggc agc cag agc atg tac tgc atc cct tgt<br>Ser Gly Phe Ile Arg Asn Gly Ser Gln Ser Met Tyr Cys Ile Pro Cys<br>310                               315                      320 | 1017 |
| gaa ggt cct tgc ccg aag gtc tgt gag gaa gaa aag aaa aca aag acc<br>Glu Gly Pro Cys Pro Lys Val Cys Glu Glu Glu Lys Lys Thr Lys Thr<br>325                           330                     335                340 | 1065 |
| att gat tct gtt act tct gct cag atg ctc caa gga tgc acc atc ttc<br>Ile Asp Ser Val Thr Ser Ala Gln Met Leu Gln Gly Cys Thr Ile Phe<br>                            345                     350                     355 | 1113 |
| aag ggc aat ttg ctc att aac atc cga cgg ggg aat aac att gct tca<br>Lys Gly Asn Leu Leu Ile Asn Ile Arg Arg Gly Asn Asn Ile Ala Ser<br>                  360                     365                     370 | 1161 |
| gag ctg gag aac ttc atg ggg ctc atc gag gtg gtg acg ggc tac gtg<br>Glu Leu Glu Asn Phe Met Gly Leu Ile Glu Val Val Thr Gly Tyr Val<br>375                               380                     385 | 1209 |
| aag atc cgc cat tct cat gcc ttg gtc tcc ttg tcc ttc cta aaa aac<br>Lys Ile Arg His Ser His Ala Leu Val Ser Leu Ser Phe Leu Lys Asn<br>                  390                     395                     400 | 1257 |
| ctt gag gag cag cta gaa ggg aat tac tcc ttc tac gtc ctc gac aac<br>Leu Glu Glu Gln Leu Glu Gly Asn Tyr Ser Phe Tyr Val Leu Asp Asn<br>405                               410                     415                420 | 1305 |
| cag aac ttg cag caa ctg tgg gac tgg gac cgc ctc atc cta gga cac<br>Gln Asn Leu Gln Gln Leu Trp Asp Trp Asp Arg Leu Ile Leu Gly His<br>                           425                     430                     435 | 1353 |
| cgc aac ctg acc atc aaa gca ggg aaa atg tac ttt gct ttc aat ccc<br>Arg Asn Leu Thr Ile Lys Ala Gly Lys Met Tyr Phe Ala Phe Asn Pro<br>                  440                     445                     450 | 1401 |
| aaa tta tgt gtt tcc gaa att tac cgc atg gag gaa gtg acg ggg act<br>Lys Leu Cys Val Ser Glu Ile Tyr Arg Met Glu Glu Val Thr Gly Thr<br>                         455                     460                     465 | 1449 |
| aaa ggg cgc caa agc aaa ggg gac ata aac acc agg aac aac ggg gag<br>Lys Gly Arg Gln Ser Lys Gly Asp Ile Asn Thr Arg Asn Asn Gly Glu<br>470                               475                     480 | 1497 |
| aga gcc tcc tgt gaa agt gac gtc ctg cat ttc acc tcc acc acc acg<br>Arg Ala Ser Cys Glu Ser Asp Val Leu His Phe Thr Ser Thr Thr Thr<br>485                               490                     495                500 | 1545 |
| tcg aag aat cgc atc atc ata acc tgg cac cgg tac cgg ccc cct gac<br>Ser Lys Asn Arg Ile Ile Ile Thr Trp His Arg Tyr Arg Pro Pro Asp<br>                  505                     510                     515 | 1593 |
| tac agg gat ctc atc agc ttc acc gtt tac tac aag gaa gca ccc ttt<br>Tyr Arg Asp Leu Ile Ser Phe Thr Val Tyr Tyr Lys Glu Ala Pro Phe<br>                    520                     525                     530 | 1641 |
| aag aat gtc aca gag tat gat ggg cag gat gcc tgc ggc tcc aac agc<br>Lys Asn Val Thr Glu Tyr Asp Gly Gln Asp Ala Cys Gly Ser Asn Ser<br>                  535                     540                     545 | 1689 |
| tgg aac atg gtg gac gtg gac ctc ccg ccc aac aag gac gtg gag ccc<br>Trp Asn Met Val Asp Val Asp Leu Pro Pro Asn Lys Asp Val Glu Pro<br>550                               555                     560 | 1737 |
| ggc atc tta cta cat ggg ctg aag ccc tgg act cag tac gcc gtt tac<br>Gly Ile Leu Leu His Gly Leu Lys Pro Trp Thr Gln Tyr Ala Val Tyr<br>565                               570                     575                580 | 1785 |
| gtc aag gct gtg acc ctc acc atg gtg gag aac gac cat atc cgt ggg<br>Val Lys Ala Val Thr Leu Thr Met Val Glu Asn Asp His Ile Arg Gly<br>                  585                     590                     595 | 1833 |
| gcc aag agt gag atc ttg tac att gcc acc aat gct tca gtt cct tcc<br>Ala Lys Ser Glu Ile Leu Tyr Ile Ala Thr Asn Ala Ser Val Pro Ser<br>                    600                     605                     610 | 1881 |
| att ccc ttg gac gtt ctt tca gca tcg aac tcc tct tct cag tta atc<br>Ile Pro Leu Asp Val Leu Ser Ala Ser Asn Ser Ser Ser Gln Leu Ile<br>615                               620                     625 | 1929 |

```
gtg aag tgg aac cct ccc tct ctg ccc aac ggc aac ctg agt tac tac   1977
Val Lys Trp Asn Pro Pro Ser Leu Pro Asn Gly Asn Leu Ser Tyr Tyr
        630                 635                 640 att gtg cgc tgg cag cgg cag cct cag gac ggc tac ctt tac cgg cac   2025
Ile Val Arg Trp Gln Arg Gln Pro Gln Asp Gly Tyr Leu Tyr Arg His
645                 650                 655                 660 aat tac tgc tcc aaa gac aaa atc ccc atc agg aag tat gcc gac ggc   2073
Asn Tyr Cys Ser Lys Asp Lys Ile Pro Ile Arg Lys Tyr Ala Asp Gly
                    665                 670                 675 acc atc gac att gag gag gtc aca gag aac ccc aag act gag gtg tgt   2121
Thr Ile Asp Ile Glu Glu Val Thr Glu Asn Pro Lys Thr Glu Val Cys
            680                 685                 690 ggt ggg gag aaa ggg cct tgc tgc gcc tgc ccc aaa act gaa gcc gag   2169
Gly Gly Glu Lys Gly Pro Cys Cys Ala Cys Pro Lys Thr Glu Ala Glu
        695                 700                 705 aag cag gcc gag aag gag gag gct gaa tac cgc aaa gtc ttt gag aat   2217
Lys Gln Ala Glu Lys Glu Glu Ala Glu Tyr Arg Lys Val Phe Glu Asn
710                 715                 720 ttc ctg cac aac tcc atc ttc gtg ccc aga cct gaa agg aag cgg aga   2265
Phe Leu His Asn Ser Ile Phe Val Pro Arg Pro Glu Arg Lys Arg Arg
725                 730                 735                 740 gat gtc atg caa gtg gcc aac acc acc atg tcc agc cga agc agg aac   2313
Asp Val Met Gln Val Ala Asn Thr Thr Met Ser Ser Arg Ser Arg Asn
            745                 750                 755 acc acg gcc gca gac acc tac aac atc acc gac ccg gaa gag ctg gag   2361
Thr Thr Ala Ala Asp Thr Tyr Asn Ile Thr Asp Pro Glu Glu Leu Glu
        760                 765                 770 aca gag tac cct ttc ttt gag agc aga gtg gat aac aag gag aga act   2409
Thr Glu Tyr Pro Phe Phe Glu Ser Arg Val Asp Asn Lys Glu Arg Thr
    775                 780                 785 gtc att tct aac ctt cgg cct ttc aca ttg tac cgc atc gat atc cac   2457
Val Ile Ser Asn Leu Arg Pro Phe Thr Leu Tyr Arg Ile Asp Ile His
790                 795                 800 agc tgc aac cac gag gct gag aag ctg ggc tgc agc gcc tcc aac ttc   2505
Ser Cys Asn His Glu Ala Glu Lys Leu Gly Cys Ser Ala Ser Asn Phe
805                 810                 815                 820 gtc ttt gca agg act atg ccc gca gaa gga gca gat gac att cct ggg   2553
Val Phe Ala Arg Thr Met Pro Ala Glu Gly Ala Asp Asp Ile Pro Gly
            825                 830                 835 cca gtg acc tgg gag cca agg cct gaa aac tcc atc ttt tta aag tgg   2601
Pro Val Thr Trp Glu Pro Arg Pro Glu Asn Ser Ile Phe Leu Lys Trp
        840                 845                 850 ccg gaa cct gag aat ccc aat gga ttg att cta atg tat gaa ata aaa   2649
Pro Glu Pro Glu Asn Pro Asn Gly Leu Ile Leu Met Tyr Glu Ile Lys
    855                 860                 865 tac gga tca caa gtt gag gat cag cga gaa tgt gtg tcc aga cag gaa   2697
Tyr Gly Ser Gln Val Glu Asp Gln Arg Glu Cys Val Ser Arg Gln Glu
870                 875                 880 tac agg aag tat gga ggg gcc aag cta aac cgg cta aac ccg ggg aac   2745
Tyr Arg Lys Tyr Gly Gly Ala Lys Leu Asn Arg Leu Asn Pro Gly Asn
885                 890                 895                 900 tac aca gcc cgg att cag gcc aca tct ctc tct ggg aat ggg tcg tgg   2793
Tyr Thr Ala Arg Ile Gln Ala Thr Ser Leu Ser Gly Asn Gly Ser Trp
            905                 910                 915 aca gat cct gtg ttc ttc tat gtc cag gcc aaa aca gga tat gaa aac   2841
Thr Asp Pro Val Phe Phe Tyr Val Gln Ala Lys Thr Gly Tyr Glu Asn
        920                 925                 930 ttc atc cat ctg atc atc gct ctg ccc gtc gct gtc ctg ttg atc gtg   2889
Phe Ile His Leu Ile Ile Ala Leu Pro Val Ala Val Leu Leu Ile Val
```

```
                    935                 940                 945
gga  ggg  ttg  gtg  att  atg  ctg  tac  gtc  ttc  cat  aga  aag  aga  aat  aac          2937
Gly  Gly  Leu  Val  Ile  Met  Leu  Tyr  Val  Phe  His  Arg  Lys  Arg  Asn  Asn
               950                      955                      960 agc  agg  ctg  ggg  aat  gga  gtg  ctg  tat  gcc  tct  gtg  aac  ccg  gag  tac          2985
Ser  Arg  Leu  Gly  Asn  Gly  Val  Leu  Tyr  Ala  Ser  Val  Asn  Pro  Glu  Tyr
965                      970                      975                      980 ttc  agc  gct  gct  gat  gtg  tac  gtt  cct  gat  gag  tgg  gag  gtg  gct  cgg          3033
Phe  Ser  Ala  Ala  Asp  Val  Tyr  Val  Pro  Asp  Glu  Trp  Glu  Val  Ala  Arg
                    985                      990                      995 gag  aag  atc  acc  atg  agc  cgg  gaa  ctt  ggg  cag  ggg  tcg  ttt  ggg               3078
Glu  Lys  Ile  Thr  Met  Ser  Arg  Glu  Leu  Gly  Gln  Gly  Ser  Phe  Gly
               1000                     1005                     1010 atg  gtc  tat  gaa  gga  gtt  gcc  aag  ggt  gtg  gtg  aaa  gat  gaa  cct               3123
Met  Val  Tyr  Glu  Gly  Val  Ala  Lys  Gly  Val  Val  Lys  Asp  Glu  Pro
          1015                     1020                     1025 gaa  acc  aga  gtg  gcc  att  aaa  aca  gtg  aac  gag  gcc  gca  agc  atg               3168
Glu  Thr  Arg  Val  Ala  Ile  Lys  Thr  Val  Asn  Glu  Ala  Ala  Ser  Met
          1030                     1035                     1040 cgt  gag  agg  att  gag  ttt  ctc  aac  gaa  gct  tct  gtg  atg  aag  gag               3213
Arg  Glu  Arg  Ile  Glu  Phe  Leu  Asn  Glu  Ala  Ser  Val  Met  Lys  Glu
          1045                     1050                     1055 ttc  aat  tgt  cac  cat  gtg  gtg  cga  ttg  ctg  ggt  gtg  gtg  tcc  caa               3258
Phe  Asn  Cys  His  His  Val  Val  Arg  Leu  Leu  Gly  Val  Val  Ser  Gln
          1060                     1065                     1070 ggc  cag  cca  aca  ctg  gtc  atc  atg  gaa  ctg  atg  aca  cgg  ggc  gat               3303
Gly  Gln  Pro  Thr  Leu  Val  Ile  Met  Glu  Leu  Met  Thr  Arg  Gly  Asp
          1075                     1080                     1085 ctc  aaa  agt  tat  ctc  cgg  tct  ctg  agg  cca  gaa  atg  gag  aat  aat               3348
Leu  Lys  Ser  Tyr  Leu  Arg  Ser  Leu  Arg  Pro  Glu  Met  Glu  Asn  Asn
          1090                     1095                     1100 cca  gtc  cta  gca  cct  cca  agc  ctg  agc  aag  atg  att  cag  atg  gcc               3393
Pro  Val  Leu  Ala  Pro  Pro  Ser  Leu  Ser  Lys  Met  Ile  Gln  Met  Ala
          1105                     1110                     1115 gga  gag  att  gca  gac  ggc  atg  gca  tac  ctc  aac  gcc  aat  aag  ttc               3438
Gly  Glu  Ile  Ala  Asp  Gly  Met  Ala  Tyr  Leu  Asn  Ala  Asn  Lys  Phe
          1120                     1125                     1130 gtc  cac  aga  gac  ctt  gct  gcc  cgg  aat  tgc  atg  gta  gcc  gaa  gat               3483
Val  His  Arg  Asp  Leu  Ala  Ala  Arg  Asn  Cys  Met  Val  Ala  Glu  Asp
          1135                     1140                     1145 ttc  aca  gtc  aaa  atc  gga  gat  ttt  ggt  atg  acg  cga  gat  atc  tat               3528
Phe  Thr  Val  Lys  Ile  Gly  Asp  Phe  Gly  Met  Thr  Arg  Asp  Ile  Tyr
          1150                     1155                     1160 gag  aca  gac  tat  tac  cgg  aaa  gga  ggg  aaa  ggg  ctg  ctg  ccc  gtg               3573
Glu  Thr  Asp  Tyr  Tyr  Arg  Lys  Gly  Gly  Lys  Gly  Leu  Leu  Pro  Val
          1165                     1170                     1175 cgc  tgg  atg  tct  cct  gag  tcc  ctc  aag  gat  gga  gtc  ttc  acc  act               3618
Arg  Trp  Met  Ser  Pro  Glu  Ser  Leu  Lys  Asp  Gly  Val  Phe  Thr  Thr
          1180                     1185                     1190 tac  tcg  gac  gtc  tgg  tcc  ttc  ggg  gtc  gtc  ctc  tgg  gag  atc  gcc               3663
Tyr  Ser  Asp  Val  Trp  Ser  Phe  Gly  Val  Val  Leu  Trp  Glu  Ile  Ala
          1195                     1200                     1205 aca  ctg  gcc  gag  cag  ccc  tac  cag  ggc  ttg  tcc  aac  gag  caa  gtc               3708
Thr  Leu  Ala  Glu  Gln  Pro  Tyr  Gln  Gly  Leu  Ser  Asn  Glu  Gln  Val
          1210                     1215                     1220 ctt  cgc  ttc  gtc  atg  gag  ggc  ggc  ctt  ctg  gac  aag  cca  gac  aac               3753
Leu  Arg  Phe  Val  Met  Glu  Gly  Gly  Leu  Leu  Asp  Lys  Pro  Asp  Asn
          1225                     1230                     1235 tgt  cct  gac  atg  ctg  ttt  gaa  ctg  atg  cgc  atg  tgc  tgg  cag  tat               3798
```

-continued

| | | | | | | | | | | |
|---|---|---|---|---|---|---|---|---|---|---|
| Cys | Pro | Asp | Met 1240 | Leu | Phe | Glu | Leu 1245 | Met | Arg | Met | Cys | Trp 1250 | Gln | Tyr |

```
aac  ccc  aag  atg  agg  cct  tcc  ttc  ctg  gag  atc  atc  agc  agc  atc    3843
Asn  Pro  Lys  Met  Arg  Pro  Ser  Phe  Leu  Glu  Ile  Ile  Ser  Ser  Ile
          1255                1260                 1265 aaa  gag  gag  atg  gag  cct  ggc  ttc  cgg  gag  gtc  tcc  ttc  tac  tac    3888
Lys  Glu  Glu  Met  Glu  Pro  Gly  Phe  Arg  Glu  Val  Ser  Phe  Tyr  Tyr
     1270                1275                  1280 agc  gag  gag  aac  aag  ctg  ccc  gag  ccg  gag  gag  ctg  gac  ctg  aag    3933
Ser  Glu  Glu  Asn  Lys  Leu  Pro  Glu  Pro  Glu  Glu  Leu  Asp  Leu  Lys
1285                1290                 1295 cca  gag  aac  atg  gag  agc  gtc  ccc  ctg  gac  ccc  tcg  gcc  tcc  tcg    3978
Pro  Glu  Asn  Met  Glu  Ser  Val  Pro  Leu  Asp  Pro  Ser  Ala  Ser  Ser
          1300                1305                 1310 tcc  tcc  ctg  cca  ctg  ccc  gac  aga  cac  tca  gga  cac  aag  gcc  gag    4023
Ser  Ser  Leu  Pro  Leu  Pro  Asp  Arg  His  Ser  Gly  His  Lys  Ala  Glu
     1315                1320                  1325 aac  ggc  ccc  ggc  cct  ggg  gtg  ctg  gtc  ctc  cgc  gcc  agc  ttc  gac    4068
Asn  Gly  Pro  Gly  Pro  Gly  Val  Leu  Val  Leu  Arg  Ala  Ser  Phe  Asp
1330                1335                 1340 gag  aga  cag  cct  tac  gcc  cac  atg  aac  ggg  ggc  cgc  aag  aac  gag    4113
Glu  Arg  Gln  Pro  Tyr  Ala  His  Met  Asn  Gly  Gly  Arg  Lys  Asn  Glu
          1345                1350                 1355 cgg  gcc  ttg  ccg  ctg  ccc  cag  tct  tcg  acc  tgc  tgatccttgg            4156
Arg  Ala  Leu  Pro  Leu  Pro  Gln  Ser  Ser  Thr  Cys
     1360                1365
```

| | |
|---|---|
| atcctgaatc tgtgcaaaca gtaacgtgtg cgcacgcgca gcggggtggg ggggagaga | 4216 |
| gagttttaac aatccattca caagcctcct gtacctcagt ggatcttcag ttctgccctt | 4276 |
| gctgcccgcg ggagacagct tctctgcagt aaaacacatt tgggatgttc cttttttcaa | 4336 |
| tatgcaagca gctttttatt ccctgcccaa acccttaact gacatgggcc tttaagaacc | 4396 |
| ttaatgacaa cacttaatag caacagagca cttgagaacc agtctcctca ctctgtccct | 4456 |
| gtccttccct gttctccctt tctctctcct ctctgcttca taacggaaaa ataattgcca | 4516 |
| caagtccagc tgggaagccc ttttttatcag tttgaggaag tggctgtccc tgtggcccca | 4576 |
| tccaaccact gtacacaccc gcctgacacc gtgggtcatt acaaaaaaac acgtggagat | 4636 |
| ggaaattttt acctttatct ttcacctttc tagggacatg aaatttacaa agggccatcg | 4696 |
| ttcatccaag gctgttacca ttttaacgct gcctaattt gccaaaatcc tgaactttct | 4756 |
| ccctcatcgg cccggcgctg attcctcgtg tccggaggca tgggtgagca tggcagctgg | 4816 |
| ttgctccatt tgagagacac gctggcgaca cactccgtcc atccgactgc ccctgctgtg | 4876 |
| ctgctcaagg ccacaggcac acaggtctca ttgcttctga ctagattatt atttggggga | 4936 |
| actggacaca ataggtcttt ctctcagtga aggtggggag aagctgaacc ggc | 4989 |

```
<210> SEQ ID NO 18
<211> LENGTH: 1367
<212> TYPE: PRT
<213> ORGANISM: Artificial Sequence
<220> FEATURE:
<221> NAME/KEY: misc_feature
<223> OTHER INFORMATION: Novel Sequence

<400> SEQUENCE: 18

Met Lys Ser Gly Ser Gly Gly Ser Pro Thr Ser Leu Trp Gly Leu
1               5                  10                  15

Leu Phe Leu Ser Ala Ala Leu Ser Leu Trp Pro Thr Ser Gly Glu Ile
             20                  25                  30
```

-continued

```
Cys Gly Pro Gly Ile Asp Ile Arg Asn Asp Tyr Gln Gln Leu Lys Arg
         35                  40                  45
Leu Glu Asn Cys Thr Val Ile Glu Gly Tyr Leu His Ile Leu Leu Ile
 50                  55                  60
Ser Lys Ala Glu Asp Tyr Arg Ser Tyr Arg Phe Pro Lys Leu Thr Val
65                   70                  75                  80
Ile Thr Glu Tyr Leu Leu Phe Arg Val Ala Gly Leu Glu Ser Leu
                 85                  90                  95
Gly Asp Leu Phe Pro Asn Leu Thr Val Ile Arg Gly Trp Lys Leu Phe
             100                 105                 110
Tyr Asn Tyr Ala Leu Val Ile Phe Glu Met Thr Asn Leu Lys Asp Ile
             115                 120                 125
Gly Leu Tyr Asn Leu Arg Asn Ile Thr Arg Gly Ala Ile Arg Ile Glu
         130                 135                 140
Lys Asn Ala Asp Leu Cys Tyr Leu Ser Thr Val Asp Trp Ser Leu Ile
145                 150                 155                 160
Leu Asp Ala Val Ser Asn Asn Tyr Ile Val Gly Asn Lys Pro Pro Lys
                 165                 170                 175
Glu Cys Gly Asp Leu Cys Pro Gly Thr Met Glu Glu Lys Pro Met Cys
             180                 185                 190
Glu Lys Thr Thr Ile Asn Asn Glu Tyr Asn Tyr Arg Cys Trp Thr Thr
         195                 200                 205
Asn Arg Cys Gln Lys Met Cys Pro Ser Thr Cys Gly Lys Arg Ala Cys
210                 215                 220
Thr Glu Asn Asn Glu Cys Cys His Pro Glu Cys Leu Gly Ser Cys Ser
225                 230                 235                 240
Ala Pro Asp Asn Asp Thr Ala Cys Val Ala Cys Arg His Tyr Tyr Tyr
             245                 250                 255
Ala Gly Val Cys Val Pro Ala Cys Pro Pro Asn Thr Tyr Arg Phe Glu
         260                 265                 270
Gly Trp Arg Cys Val Asp Arg Asp Phe Cys Ala Asn Ile Leu Ser Ala
         275                 280                 285
Glu Ser Ser Asp Ser Glu Gly Phe Val Ile His Asp Gly Glu Cys Met
290                 295                 300
Gln Glu Cys Pro Ser Gly Phe Ile Arg Asn Gly Ser Gln Ser Met Tyr
305                 310                 315                 320
Cys Ile Pro Cys Glu Gly Pro Cys Pro Lys Val Cys Glu Glu Lys
             325                 330                 335
Lys Thr Lys Thr Ile Asp Ser Val Thr Ser Ala Gln Met Leu Gln Gly
             340                 345                 350
Cys Thr Ile Phe Lys Gly Asn Leu Leu Ile Asn Ile Arg Arg Gly Asn
         355                 360                 365
Asn Ile Ala Ser Glu Leu Glu Asn Phe Met Gly Leu Ile Glu Val Val
         370                 375                 380
Thr Gly Tyr Val Lys Ile Arg His Ser His Ala Leu Val Ser Leu Ser
385                 390                 395                 400
Phe Leu Lys Asn Leu Glu Glu Gln Leu Glu Gly Asn Tyr Ser Phe Tyr
                 405                 410                 415
Val Leu Asp Asn Gln Asn Leu Gln Gln Leu Trp Asp Trp Asp Arg Leu
             420                 425                 430
Ile Leu Gly His Arg Asn Leu Thr Ile Lys Ala Gly Lys Met Tyr Phe
         435                 440                 445
```

-continued

Ala Phe Asn Pro Lys Leu Cys Val Ser Glu Ile Tyr Arg Met Glu Glu
450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
                485                 490                 495

Ser Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
        515                 520                 525

Glu Ala Pro Phe Lys Asn Val Thr Glu Tyr Asp Gly Gln Asp Ala Cys
530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
                565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Ala Thr Asn Ala
        595                 600                 605

Ser Val Pro Ser Ile Pro Leu Asp Val Leu Ser Ala Ser Asn Ser Ser
610                 615                 620

Ser Gln Leu Ile Val Lys Trp Asn Pro Pro Ser Leu Pro Asn Gly Asn
625                 630                 635                 640

Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
            660                 665                 670

Tyr Ala Asp Gly Thr Ile Asp Ile Glu Glu Val Thr Glu Asn Pro Lys
        675                 680                 685

Thr Glu Val Cys Gly Gly Glu Lys Gly Pro Cys Cys Ala Cys Pro Lys
690                 695                 700

Thr Glu Ala Glu Lys Gln Ala Glu Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
850                 855                 860

Tyr Glu Ile Lys Tyr Gly Ser Gln Val Glu Asp Gln Arg Glu Cys Val

-continued

```
        865                 870                 875                 880
    Ser Arg Gln Glu Tyr Arg Lys Tyr Gly Gly Ala Lys Leu Asn Arg Leu
                        885                 890                 895
    Asn Pro Gly Asn Tyr Thr Ala Arg Ile Gln Ala Thr Ser Leu Ser Gly
                900                 905                 910
    Asn Gly Ser Trp Thr Asp Pro Val Phe Phe Tyr Val Gln Ala Lys Thr
            915                 920                 925
    Gly Tyr Glu Asn Phe Ile His Leu Ile Ile Ala Leu Pro Val Ala Val
        930                 935                 940
    Leu Leu Ile Val Gly Gly Leu Val Ile Met Leu Tyr Val Phe His Arg
    945                 950                 955                 960
    Lys Arg Asn Asn Ser Arg Leu Gly Asn Gly Val Leu Tyr Ala Ser Val
                        965                 970                 975
    Asn Pro Glu Tyr Phe Ser Ala Ala Asp Val Tyr Val Pro Asp Glu Trp
                980                 985                 990
    Glu Val Ala Arg Glu Lys Ile Thr Met Ser Arg Glu Leu Gly Gln Gly
            995                 1000                1005
    Ser Phe Gly Met Val Tyr Glu Gly Val Ala Lys Gly Val Val Lys
        1010                1015                1020
    Asp Glu Pro Glu Thr Arg Val Ala Ile Lys Thr Val Asn Glu Ala
        1025                1030                1035
    Ala Ser Met Arg Glu Arg Ile Glu Phe Leu Asn Glu Ala Ser Val
        1040                1045                1050
    Met Lys Glu Phe Asn Cys His His Val Arg Leu Leu Gly Val
        1055                1060                1065
    Val Ser Gln Gly Gln Pro Thr Leu Val Ile Met Glu Leu Met Thr
        1070                1075                1080
    Arg Gly Asp Leu Lys Ser Tyr Leu Arg Ser Leu Arg Pro Glu Met
        1085                1090                1095
    Glu Asn Asn Pro Val Leu Ala Pro Pro Ser Leu Ser Lys Met Ile
        1100                1105                1110
    Gln Met Ala Gly Glu Ile Ala Asp Gly Met Ala Tyr Leu Asn Ala
        1115                1120                1125
    Asn Lys Phe Val His Arg Asp Leu Ala Ala Arg Asn Cys Met Val
        1130                1135                1140
    Ala Glu Asp Phe Thr Val Lys Ile Gly Asp Phe Gly Met Thr Arg
        1145                1150                1155
    Asp Ile Tyr Glu Thr Asp Tyr Tyr Arg Lys Gly Gly Lys Gly Leu
        1160                1165                1170
    Leu Pro Val Arg Trp Met Ser Pro Glu Ser Leu Lys Asp Gly Val
        1175                1180                1185
    Phe Thr Thr Tyr Ser Asp Val Trp Ser Phe Gly Val Val Leu Trp
        1190                1195                1200
    Glu Ile Ala Thr Leu Ala Glu Gln Pro Tyr Gln Gly Leu Ser Asn
        1205                1210                1215
    Glu Gln Val Leu Arg Phe Val Met Glu Gly Gly Leu Leu Asp Lys
        1220                1225                1230
    Pro Asp Asn Cys Pro Asp Met Leu Phe Glu Leu Met Arg Met Cys
        1235                1240                1245
    Trp Gln Tyr Asn Pro Lys Met Arg Pro Ser Phe Leu Glu Ile Ile
        1250                1255                1260
    Ser Ser Ile Lys Glu Glu Met Glu Pro Gly Phe Arg Glu Val Ser
        1265                1270                1275
```

-continued

```
Phe Tyr Tyr Ser Glu Glu Asn Lys Leu Pro Glu Pro Glu Glu Leu
    1280            1285                1290

Asp Leu Lys Pro Glu Asn Met Glu Ser Val Pro Leu Asp Pro Ser
    1295            1300                1305

Ala Ser Ser Ser Ser Leu Pro Leu Pro Asp Arg His Ser Gly His
    1310            1315                1320

Lys Ala Glu Asn Gly Pro Gly Pro Gly Val Leu Val Leu Arg Ala
    1325            1330                1335

Ser Phe Asp Glu Arg Gln Pro Tyr Ala His Met Asn Gly Gly Arg
    1340            1345                1350

Lys Asn Glu Arg Ala Leu Pro Leu Pro Gln Ser Ser Thr Cys
    1355            1360                1365
```